(12) United States Patent
Cowe

(10) Patent No.: US 9,814,836 B2
(45) Date of Patent: Nov. 14, 2017

(54) AUTOINJECTORS

(75) Inventor: Toby Cowe, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 1242 days.

(21) Appl. No.: 13/824,911

(22) PCT Filed: Sep. 13, 2011

(86) PCT No.: PCT/GB2011/051710
§ 371 (c)(1),
(2), (4) Date: Apr. 10, 2013

(87) PCT Pub. No.: WO2012/038721
PCT Pub. Date: Mar. 29, 2012

(65) Prior Publication Data
US 2013/0218128 A1    Aug. 22, 2013

Related U.S. Application Data

(60) Provisional application No. 61/384,746, filed on Sep. 21, 2010.

(30) Foreign Application Priority Data

Sep. 21, 2010  (GB) .................................. 1015799.8
Sep. 22, 2010  (GB) .................................. 1015905.1

(51) Int. Cl.
*A61M 5/20*  (2006.01)
*A61M 5/24*  (2006.01)
(Continued)

(52) U.S. Cl.
CPC ............ *A61M 5/2033* (2013.01); *A61M 5/24* (2013.01); *A61M 5/3204* (2013.01);
(Continued)

(58) Field of Classification Search
CPC ............ A61M 5/2033; A61M 5/31583; A61M 5/326; A61M 2005/202; A61M 2005/206;
(Continued)

(56) References Cited

U.S. PATENT DOCUMENTS 5,709,662 A * 1/1998 Olive .................. A61M 5/2033
                                              604/110
6,099,503 A * 8/2000 Stradella ............. A61M 5/2033
                                              604/131
(Continued)

FOREIGN PATENT DOCUMENTS

CH      696 261 A5    3/2007
EP      0666084 A2    8/1995
(Continued)

OTHER PUBLICATIONS

GB Search Report, dated Jan. 28, 2011, corresponding from GB application.
(Continued)

*Primary Examiner* — Andrew Gilbert
(74) *Attorney, Agent, or Firm* — Young & Thompson

(57) ABSTRACT

An autoinjector includes a housing for receiving in use in a generally longitudinal loading direction a syringe assembly including a syringe carrier and a syringe, the syringe including a syringe body having a slideable internal piston for expressing a dose contained in the body through a needle at a forward end thereof; a drive mechanism for providing drive for operation of the autoinjector and being disposed generally within the housing and including a mechanical energy source and a winder element for being rotated to charge the energy source, and an input transmission train operational between the syringe assembly and the winder
(Continued)

element in use, whereby loading of the syringe assembly into the housing rotates the winder element to charge the energy source.

17 Claims, 31 Drawing Sheets

(51) Int. Cl.
*A61M 5/32* (2006.01)
*A61M 5/315* (2006.01)

(52) U.S. Cl.
CPC ......... *A61M 5/31583* (2013.01); *A61M 5/326* (2013.01); *A61M 2005/202* (2013.01); *A61M 2005/206* (2013.01); *A61M 2005/2407* (2013.01); *A61M 2005/2411* (2013.01); *A61M 2005/3247* (2013.01)

(58) Field of Classification Search
CPC .. A61M 2005/2407; A61M 2005/2411; A61M 2005/3247
See application file for complete search history.

(56) References Cited

U.S. PATENT DOCUMENTS

| | | | | |
|---|---|---|---|---|
| 6,454,743 | B1* | 9/2002 | Weber | A61M 5/2033 604/131 |
| 7,678,084 | B2* | 3/2010 | Judson | A61M 5/24 604/110 |
| 8,647,303 | B2* | 2/2014 | Cowe | A61M 5/20 604/134 |
| 8,932,266 | B2* | 1/2015 | Wozencroft | A61M 5/2033 604/110 |
| 9,061,103 | B2* | 6/2015 | Kemp | A61M 5/002 |
| 9,242,053 | B2* | 1/2016 | Wozencroft | A61M 5/2033 |
| 2004/0267199 | A1 | 12/2004 | Marshall et al. | |
| 2005/0020979 | A1 | 1/2005 | Westbye et al. | |
| 2005/0273055 | A1* | 12/2005 | Harrison | A61M 5/326 604/136 |
| 2006/0089593 | A1 | 4/2006 | Landau et al. | |
| 2009/0259181 | A1* | 10/2009 | Moser | A61M 5/2448 604/135 |
| 2011/0028910 | A1 | 2/2011 | Weber | |
| 2011/0106018 | A1 | 5/2011 | Rufer et al. | |
| 2011/0144584 | A1* | 6/2011 | Wozencroft | A61M 5/2033 604/110 |
| 2011/0196339 | A1 | 8/2011 | Hirschel et al. | |
| 2012/0172815 | A1* | 7/2012 | Holmqvist | A61M 5/20 604/208 |
| 2012/0279329 | A1* | 11/2012 | Veasey | A61M 5/31535 74/34 |
| 2013/0123697 | A1* | 5/2013 | Ekman | A61M 5/2033 604/110 |
| 2013/0138049 | A1* | 5/2013 | Kemp | A61M 5/2033 604/197 |
| 2013/0281936 | A1* | 10/2013 | Kemp | A61M 5/002 604/197 |

FOREIGN PATENT DOCUMENTS

| | | |
|---|---|---|
| EP | 1 392 377 B1 | 3/2004 |
| EP | 2 050 477 A1 | 12/2004 |
| EP | 2 080 532 A1 | 7/2009 |
| WO | 88/10383 A1 | 12/1988 |
| WO | 94/21316 A1 | 9/1994 |
| WO | 2004/108193 A1 | 12/2004 |
| WO | 2005/079889 A1 | 9/2005 |
| WO | 2007066152 A2 | 6/2007 |
| WO | 2008/148518 A1 | 12/2008 |
| WO | 2008/155144 A1 | 12/2008 |
| WO | 2009007305 A1 | 1/2009 |
| WO | 2009/098502 A2 | 8/2009 |
| WO | 2009/141650 A2 | 11/2009 |
| WO | 2010017650 A1 | 2/2010 |
| WO | 2010026414 A1 | 3/2010 |
| WO | 2010053569 A1 | 5/2010 |
| WO | 2010070038 A2 | 6/2010 |
| WO | 2010/076569 A2 | 7/2010 |
| WO | 2010/076792 A1 | 7/2010 |

OTHER PUBLICATIONS

GB Search Report, dated Feb. 25, 2011, corresponding from GB application.
International Search Report, dated Jul. 4, 2012, from corresponding PCT application.

\* cited by examiner

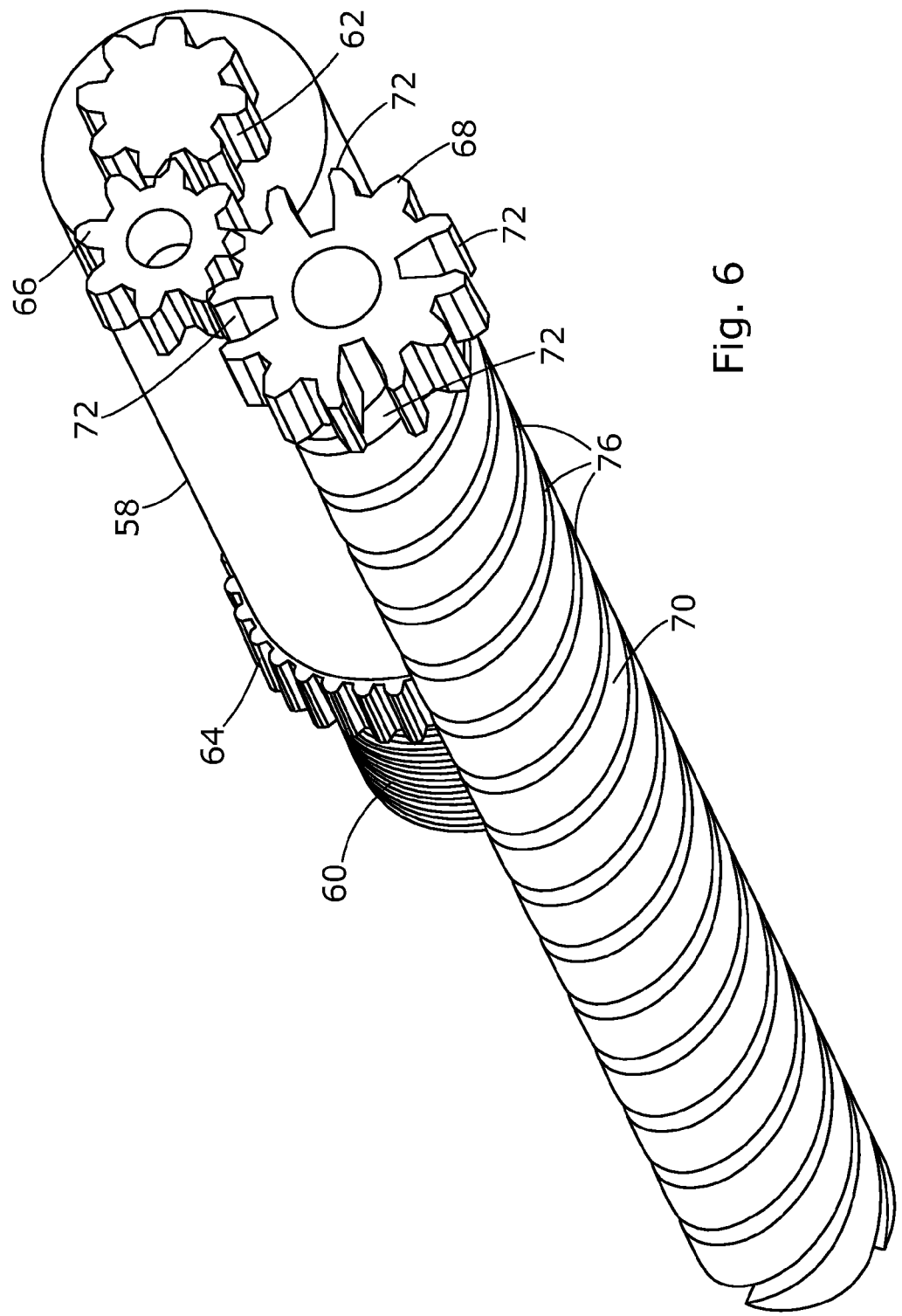

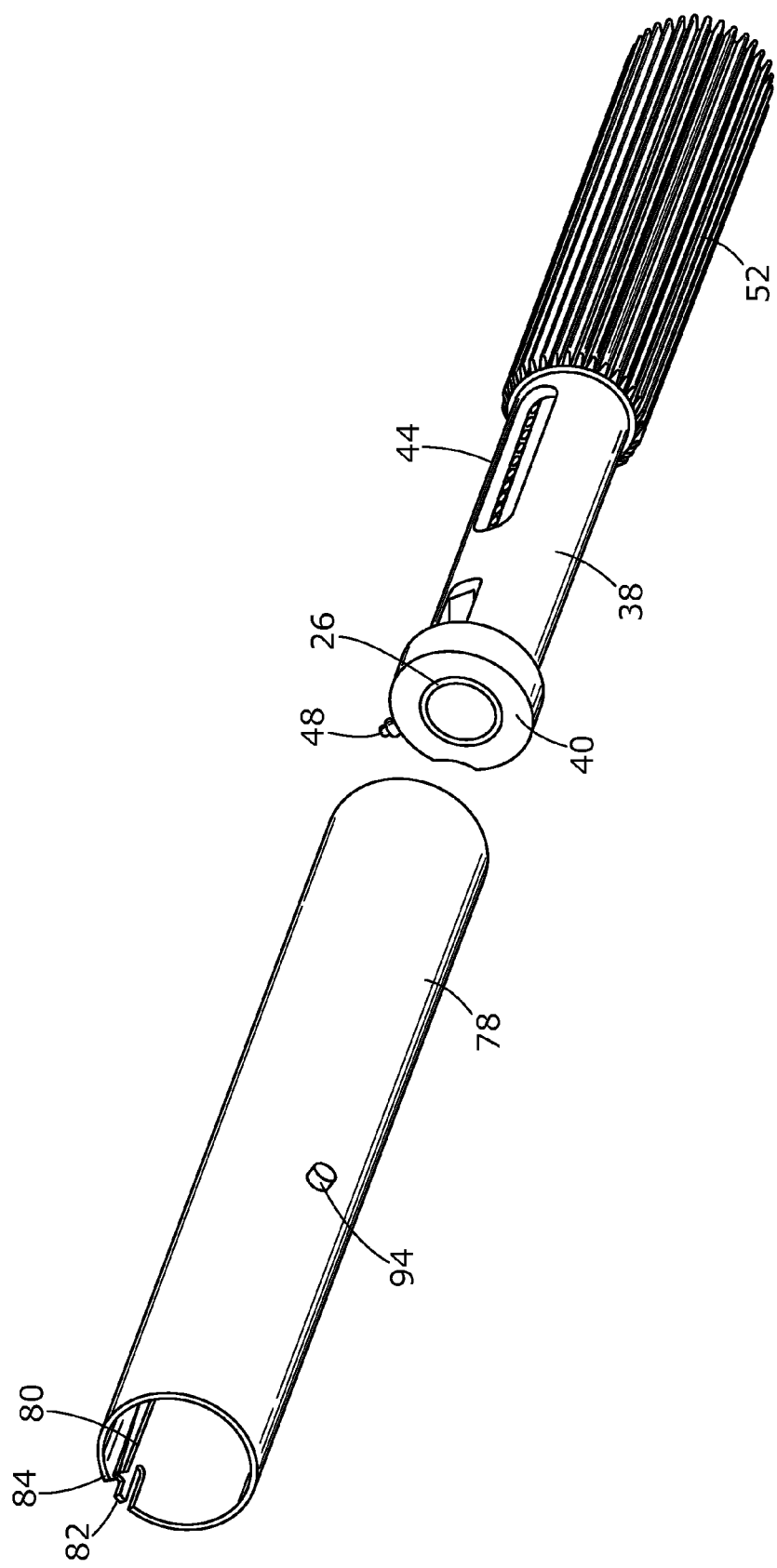

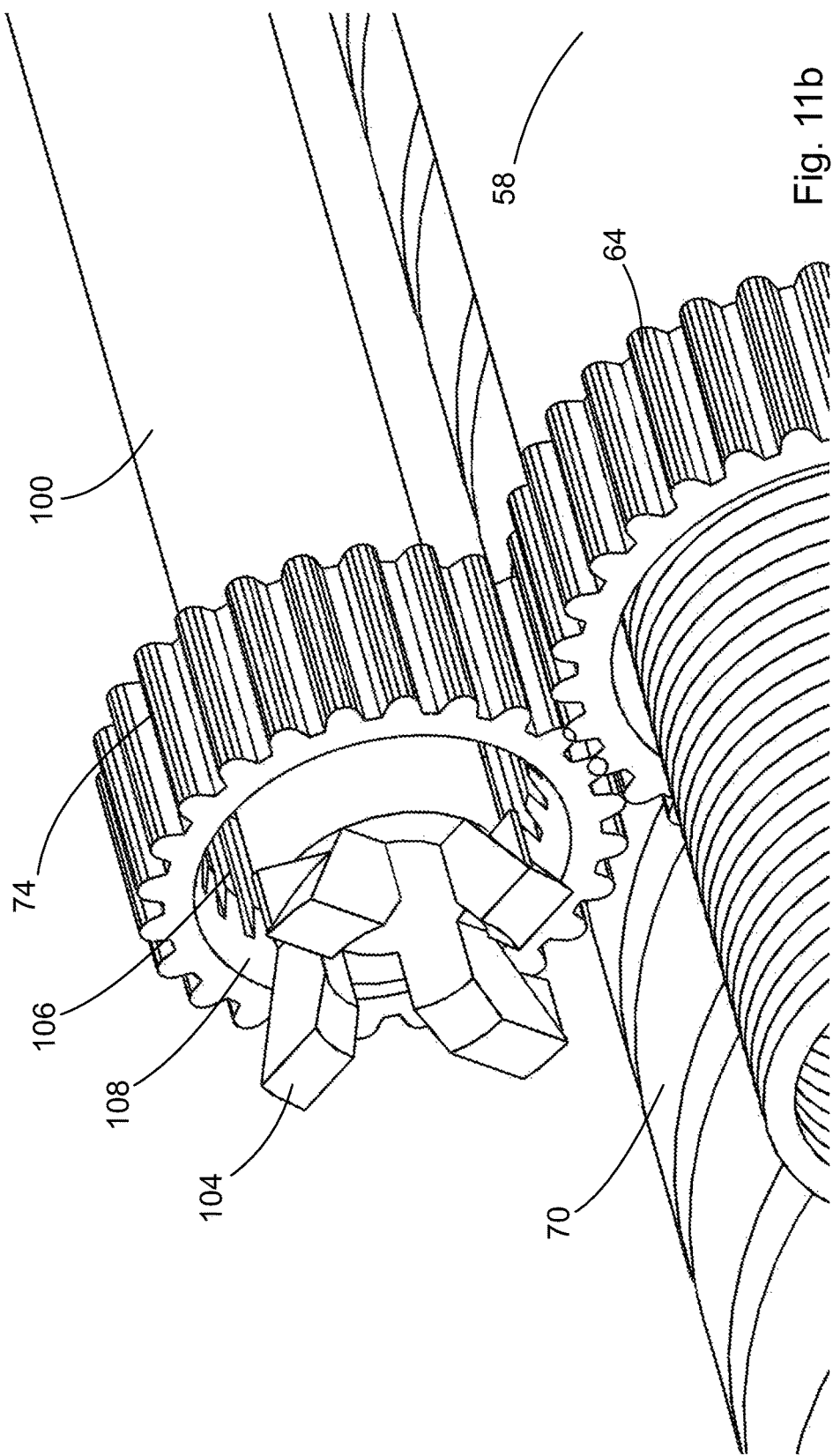

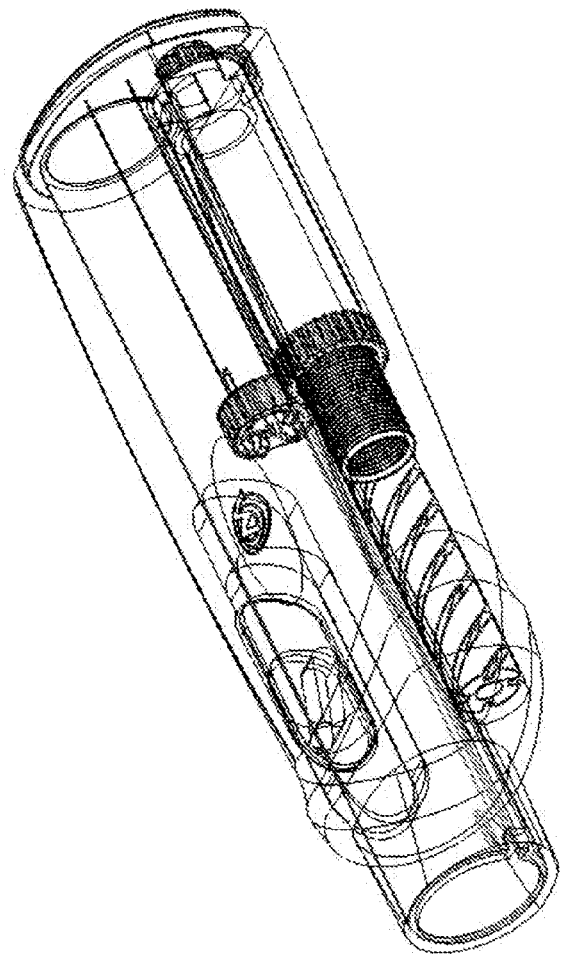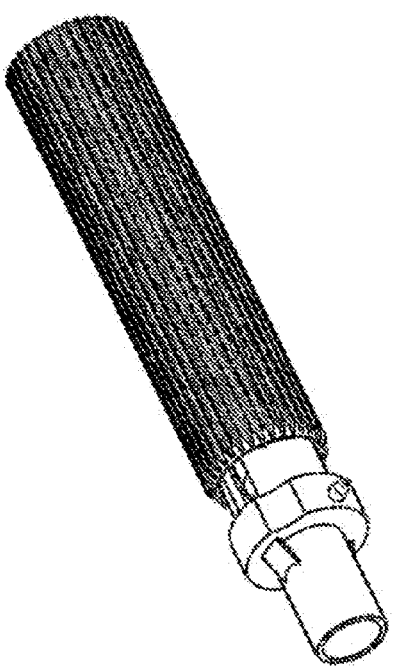
Fig. 14(d)

AUTOINJECTORS

This invention relates to autoinjectors and in particular, but not exclusively, to reusable autoinjectors which in use are loaded with a disposable syringe assembly containing a syringe with the medicament to be injected, and which operate to urge the syringe needle into an injection site and then express a dose.

BACKGROUND OF THE INVENTION

In such devices the designer has a choice as to the amount of functionality carried in the syringe assembly and that in the reusable part of autoinjector. Generally greater functionality in the syringe assembly increases the complexity and/or component count although other factors are important such as safety, comfort and ease of use. Where, as is often the case, a reusable device has no internal power source for the drive mechanism, the drive mechanism must be primed or charged during an arming operation. In a known type of reusable device such as disclosed in EP0666084 there is a direct 1:1 relationship between the force to prime the spring and the force delivered by the spring. This means that the user has to input same magnitude of force into the device to arm it. This can be problematic because if quite a strong force is required it may be beyond what the user can easily apply safely without slipping. But of equal if not greater significance is that, particularly for apprehensive users, an arming process which requires application of a strong force may suggest a powerful or fierce injection operation. There is therefore a need for an autoinjector in which a soft arming force is effective.

SUMMARY OF THE INVENTION

Accordingly, in one aspect this invention provides an autoinjector comprising:
 a housing for receiving in use in a generally longitudinal loading direction a syringe assembly comprising a syringe carrier and a syringe, the syringe including a syringe body having a slideable internal piston for expressing a dose contained in the body through a needle at a forward end thereof;
 a drive mechanism for providing drive for operation of the autoinjector and being disposed generally within said housing and including a mechanical energy source and a winder element for being rotated to charge the energy source, and
 an input transmission train operational between the syringe assembly and the winder element in use, whereby loading of said syringe assembly into said housing rotates said winder element to charge the energy source.

By this arrangement an energy source, for example a rotary energy source, may be wound by applying a relatively low insertion force over a relatively long stroke to provide the mechanical work to charge the energy source. Also converting the linear injection force into a rotary winding movement means that the energy source can drive the mechanism through a different transmission train.

Although the housing could be open, it is preferred for it to generally enclose a passage for receiving in use said syringe assembly. The passage may be designed so that in use said syringe assembly is inserted forwardly with said passage through a rear end. Alternatively, it may be designed so that, in use said syringe assembly is inserted rearwardly into said passage through a front end. A wide variety of transmission trains may be used to provide linear to rotary conversion, but said input transmission train may comprise a longitudinal screw element mounted for rotation and engaged by a complementary element such as a tooth or a threaded element, that moves linearly in use upon insertion of said syringe assembly into said housing, whereby linear movement of said screw element induces rotation of said screw element. Other gearing arrangements may be used; for example, a rack and pinion type arrangement could be used, with the use of helical or bevel gears where appropriate.

The screw element may include a thread of uniform pitch, or the screw element may include a thread of non-uniform pitch to provide desired variable force: displacement profiles.

The complementary element may be drivingly connected directly or indirectly to said winder element depending on the particular design. Thus, in some embodiments, the complementary element may be a part of said winder element; in others it may be connected by a gear train.

The rotary energy source may take many forms, it may be a torsion spring; or it may include a constant torque spring, for example operating as a constant torque motor. Alternatively, it could comprise in combination a generally linear acting compressible or expandable element or material and a linear to rotary motion converter.

As noted above, an important feature of particular embodiments is that the transmission characteristics of the mechanism charging the energy source may be designed to be different to those of the mechanisms transmitting the energy into the drive mechanism. Accordingly the device preferably includes an output transmission train connected to said rotary energy source which is different to and/or separate from said input transmission train.

The overall mechanical advantage of the combined input and output transmission trains may therefore be non-unity, and advantageously is greater than unity, whereby the source is charged by moving a relatively low force through a relatively large distance, and causes said drive mechanism to provide a relatively large force over a relatively short stroke.

Preferably the input transmission train includes a tooth element for moving linearly in use with the syringe assembly and engaged in a helical thread. Where there are separate input and output transmission trains, it may be convenient to design them so that, upon loading of the syringe assembly in use into the autoinjector, the input transmission train is interrupted or disengaged before said output transmission train engages or becomes operational.

Where said syringe assembly includes a removable needle shield initially engaging the syringe to cover the syringe needle, the device preferably includes a needle shield remover for being moved to remove the needle shield upon loading of the syringe assembly into the autoinjector.

In another aspect, this invention provides an autoinjector comprising:
 a housing for receiving in use in a generally longitudinal loading direction a syringe assembly comprising a syringe carrier and a syringe, the syringe including a syringe body having a slideable internal piston for expressing a dose contained in the body through a needle at a forward end thereof;
 a drive mechanism for providing drive for operation of the autoinjector and being disposed generally within said housing and including a mechanical energy source and a charger element for being moved to charge the mechanical energy source;
 an input transmission train operational between the syringe assembly and said charger element in use whereby loading of said syringe assembly into said housing moves said charger element to charge said source, and an output transmission train operational between the energy source and said drive mechanism to power said drive mechanism, wherein said input transmission train and said output transmission train including at least some different elements.

It will of course be appreciated that the mechanical energy source may take many forms including, but not limited to, compression springs, tension springs, torsion springs, and constant force and constant torque springs.

In another aspect this invention provides an autoinjector comprising:

a housing containing a drive mechanism and adapted in use to provide drive motion to a syringe assembly via a drive train including a gear train, wherein one of the gears in the gear train is mounted on a shaft for movement between:
 a) a ratchet position in which the gear is constrained to allow rotation in a single direction only
 b) a braking position where a variable retarding friction force is applied to the gear wheel, and
 c) a release position in which the gear wheel may rotate generally freely.

In another aspect the invention provides a syringe assembly comprising a housing generally containing a syringe, and a resiliently biased syringe needle shield adapted to lock out in a needle shielding position upon completion of an injection.

In another aspect, this invention provides a syringe assembly comprising a syringe and a syringe housing comprising forward and rearward parts, at least one of said parts including an integral formed biasing element. Preferably said biasing element is found on the forward part. Preferably the forward part comprises a front shielding portion connected by resilient bias means to a rear support portion. Preferably the rear support portion includes means for releasably latching with said rear part of the syringe housing initially to hold the syringe in a rearward position in the housing.

In another aspect this invention provides a syringe assembly comprising a syringe housing generally containing a syringe, and a plunger device threadedly engaged with said syringe housing whereby rotation of the plunger relative to the housing moves the plunger forwardly into the syringe.

In another aspect this invention provides syringe shield formed of moulded plastics material, having first and second generally cylindrical portions bridged by an integral resiliently compressible and/or extendable portion, the device being adapted to receive in use a syringe.

In another aspect this invention provides a method of autoinjection which comprises inserting a disposable syringe assembly into an autoinjector main unit to thereby charge a mechanical energy source within said unit and thereafter releasing said energy source to effect autoinjection. Where the syringe carries a needle shield said inserting action is preferably also effective to release the needle shield from the needle.

Although in the illustrated embodiments the autoinjector effects automatic insertion and expulsion of a dose, it will be appreciated that the invention may readily be adapted to provide just one of these actions rather than both.

Whilst the invention has been described above, it extends to any inventive combination or sub-combination of the features disclosed in the following description, drawings or claims.

BRIEF DESCRIPTION OF THE DRAWINGS

The invention may be performed in various ways, and, by way of example only, two specific embodiments thereof will now be described, reference being made to the accompanying drawings, in which:

FIG. 6 is a detailed view showing the input transmission train between the screw and the drive shaft of the drive mechanism;

FIG. 8 is a perspective view of a sleeve in the main autoinjector housing, which slideably receives the syringe assembly, and the syringe assembly;

DETAILED DESCRIPTION OF THE PREFERRED EMBODIMENTS

Referring initially to the first embodiment of FIGS. 1 to 15, the disclosed autoinjector comprises a reusable drive unit 10 into which is loaded longitudinally from the rear a syringe assembly 12 as to be described in detail below. The drive unit 10 contains a spring-driven drive mechanism for providing drive for operation of the autoinjector. The drive mechanism is mechanically charged by harnessing and converting the linear motion as the syringe assembly is pushed home into the drive unit, to charge the drive mechanism.

Figure 2:
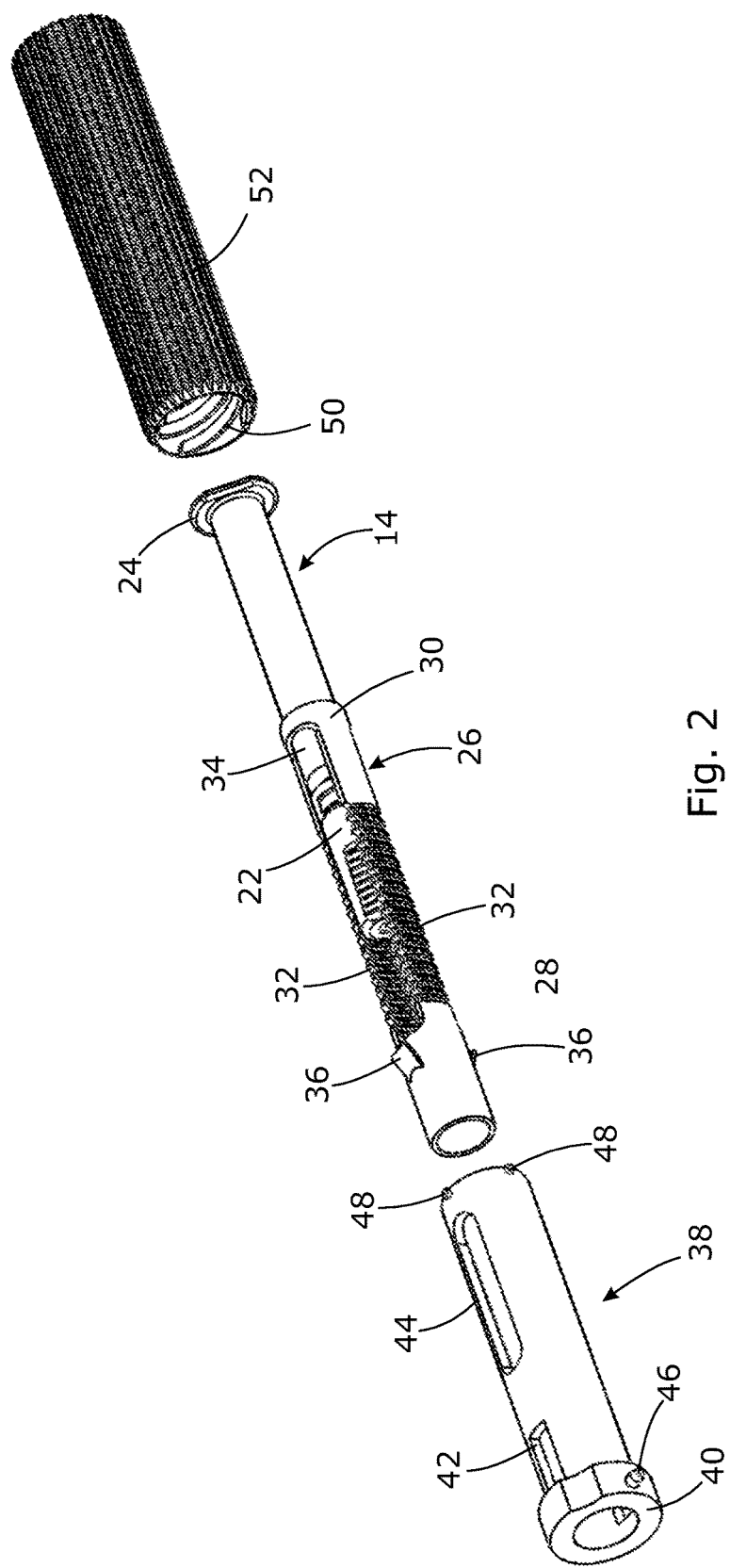
FIG. 2 is an exploded view of the syringe assembly of FIG. 1.
Figure 3:
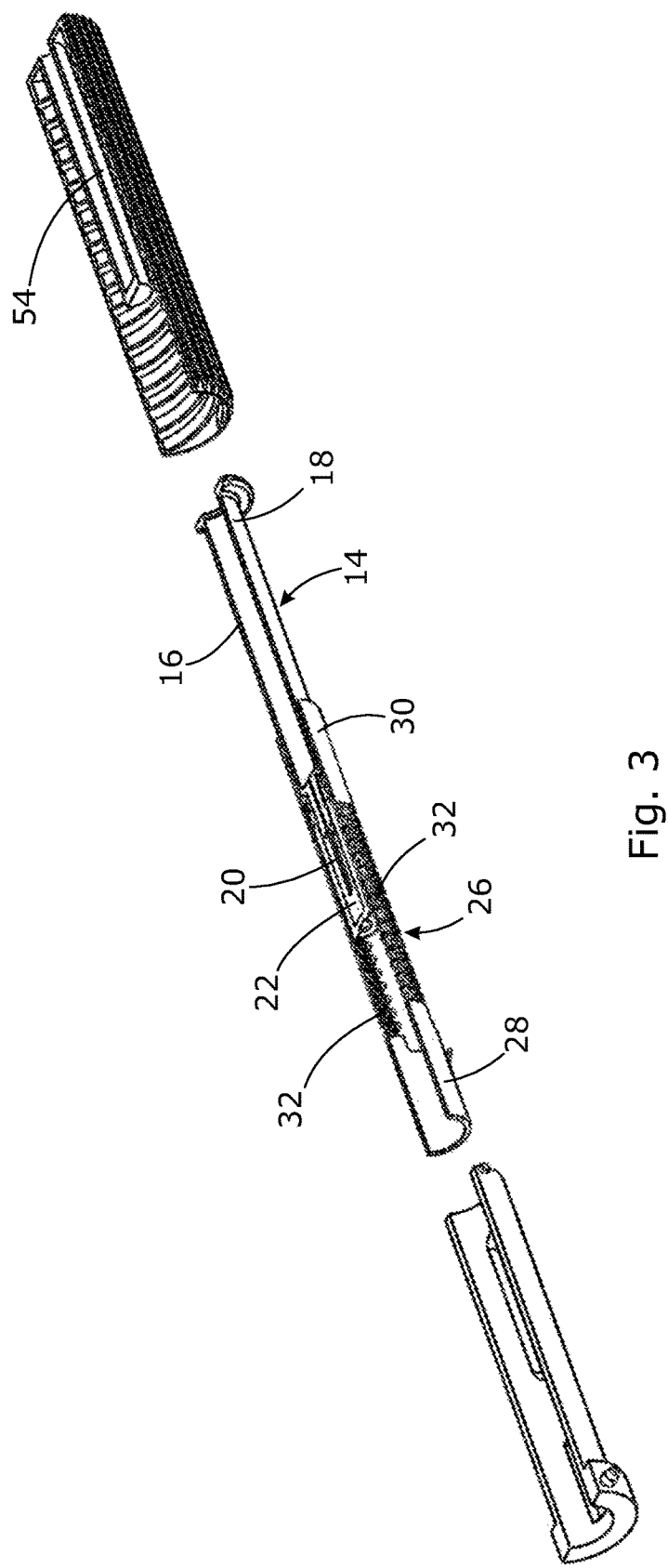
FIG. 3 is a view of the syringe assembly similar to FIG. 2, but in section.

Referring to FIGS. 2 and 3, the syringe assembly comprises a syringe 14 of conventional form having a tubular body 16, and a slideable piston 18 for expressing a dose through a needle 20 at the forward end of the syringe body 16. The needle may be covered with a rigid needle shield 22 to keep the needle sterile and prevent evaporation of the medicament. The syringe body 16 has an outwardly directed flange 24 at its rear end. Fitting concentrically around the syringe is a one-piece moulded plastics syringe shield 26 comprising inextensible forward and rearward portions 28, 30 respectively bridged by twin concertina connecting spring portions 32 which allow the syringe shield 26 to be compressed and foreshorten from the relaxed position shown in FIGS. 2 and 3. As seen more clearly in FIG. 2, the syringe shield 26 is cut away at the sides to provide opposed apertures 34. On the forward part 28 of the syringe shield are provided diametrically opposed, rearwardly directed flexible barbs 36 which provide a retaining and lock out feature to be described below.

The syringe 14 and syringe shield 16 are slideably contained within a syringe carrier 38 for sliding movement. The syringe carrier 38 is of generally cylindrical form having a flange 40 at its front end, a pair of diametrically opposed apertures 42 in which the rearwardly directed barbs 36 on the syringe shield 26 are received prior to use of the assembly. A rearward pair of diametrically opposed apertures 44 are aligned with the apertures 34 in the syringe shield 26 to allow the contents of the syringe, and the position of the piston 18 to be visually assessed prior to, during and after use.

Projecting radially from the flange 40 is a single drive peg 46 which forms one part of a linear to rotary transmission coupling with the drive mechanism as to be described below. At its rear end, the syringe carrier carries four equi-spaced radial lugs 48 which engage corresponding threads of a 4-start internal threaded portion 50 on the inner surface of a plunger 52. The plunger is of generally cylindrical form with a closed end with the outer cylindrical surface being longitudinally splined to allow engagement with the drive mechanism to be described below. As can be seen in FIG. 3, the plunger 52 includes a central drive rod 54 designed in use to enter into the open rear end of the syringe body 16 to contact the plunger.

In use, assuming the flange 40 is pressing against an injection site, rotating the plunger 52 in the appropriate sense relative to the syringe carrier 38 initially moves the syringe 14 and syringe shield 26 forwardly relative to the syringe carrier 38 so that the syringe needle penetrates the injection site. The forward portion 28 of the syringe shield 26 is prevented from moving beyond the forward end of the flange by the contact with the injection site, and the spring portions 32 compress as the rearward part 26 is pushed forwardly by the syringe flange 24. Once the syringe has reached its forwardmost position, continued movement of the plunger causes the drive rod 54 to move the piston 18 to express a dose. On completion of the injection, removal of the flange 40 from the injection site releases the forward constraint on the needle shield 26 so that the forward part 28 is pushed forwardly beyond the end of the flange 40 by the springs 32 and locks there as the resilient barbs 36 snap past the end face of flange 40.

Figure 4:
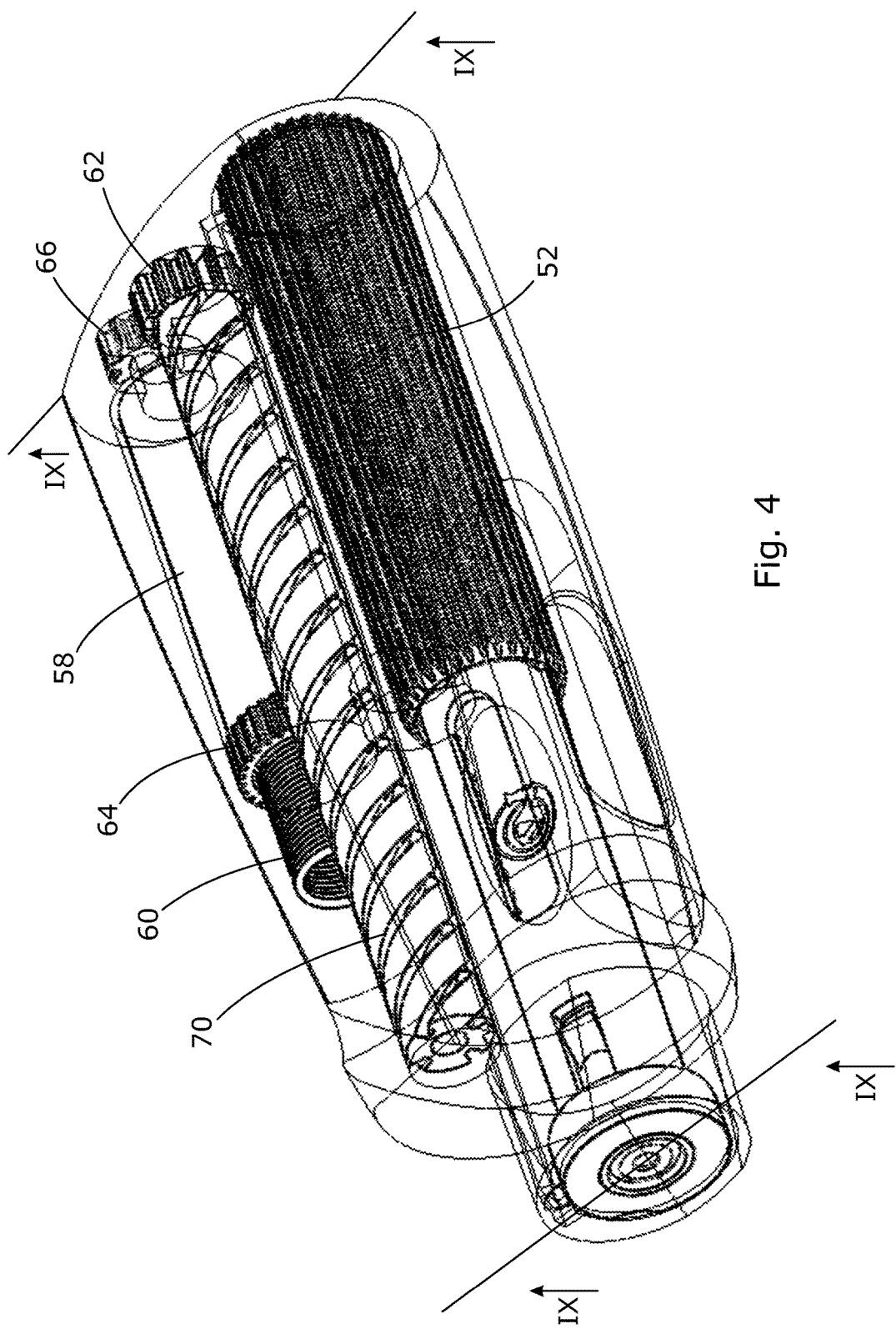
FIG. 4 is a view of the autoinjector of FIG. 1 from below, with the syringe assembly having been fully inserted, and the housing shown in phantom, particularly to illustrate the transmission train between the syringe assembly and the drive spring during charging of the drive spring.
Figure 5:
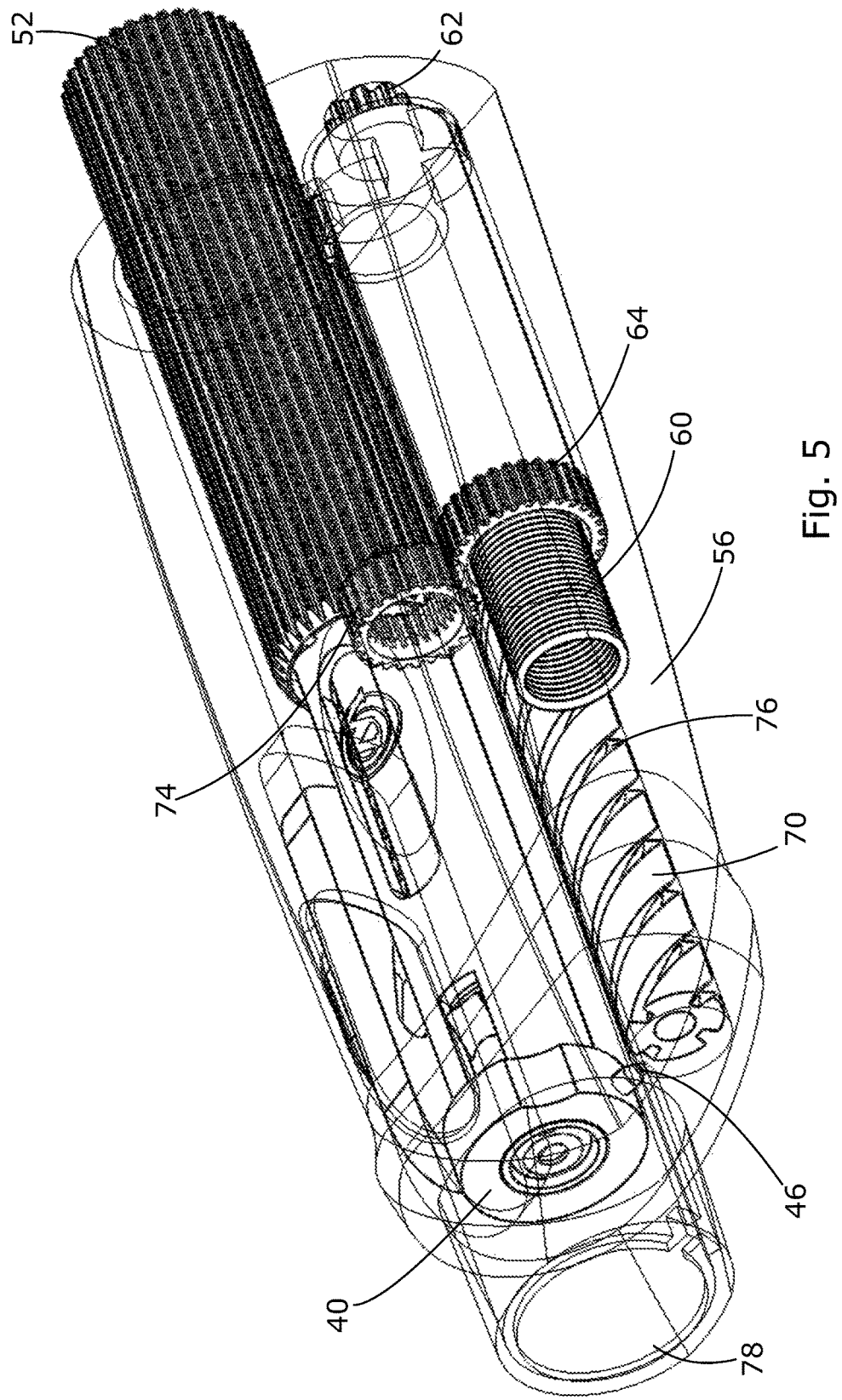
FIG. 5 is a view similar to FIG. 4 but from above and with the syringe assembly nearing its fully inserted position, in order to show certain elements making up the transmission train between the drive mechanism and the plunger of the syringe assembly.
Figure 7A:
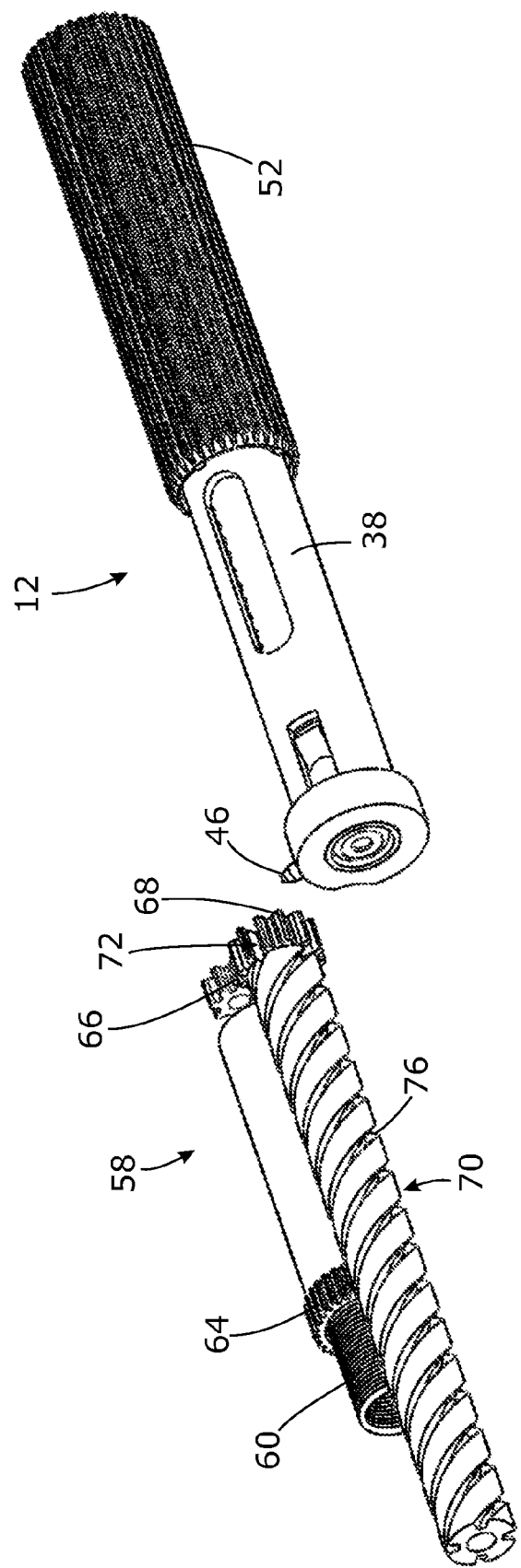
FIGS. 7($a$), ($b$), ($c$) and ($d$) are respective views showing just the syringe assembly and certain parts of the drive mechanism prior to insertion of the syringe assembly, just after insertion, part way through insertion, and when the syringe assembly is fully home, respectively.
Figure 7B:
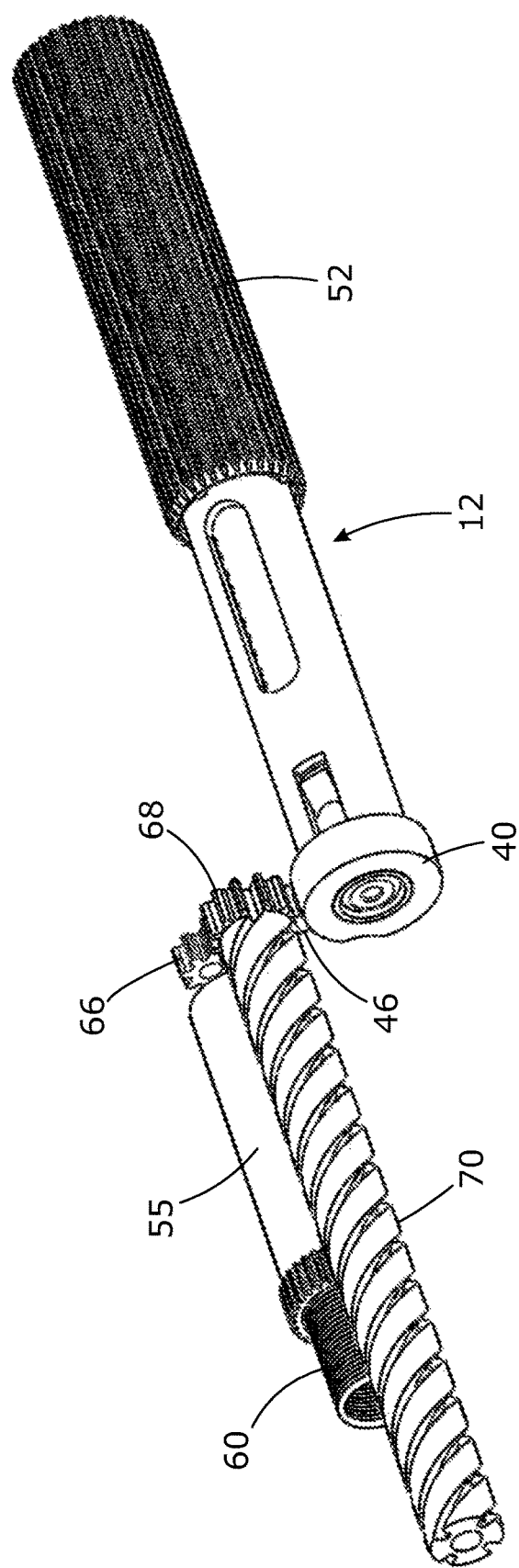
Figure 7C:
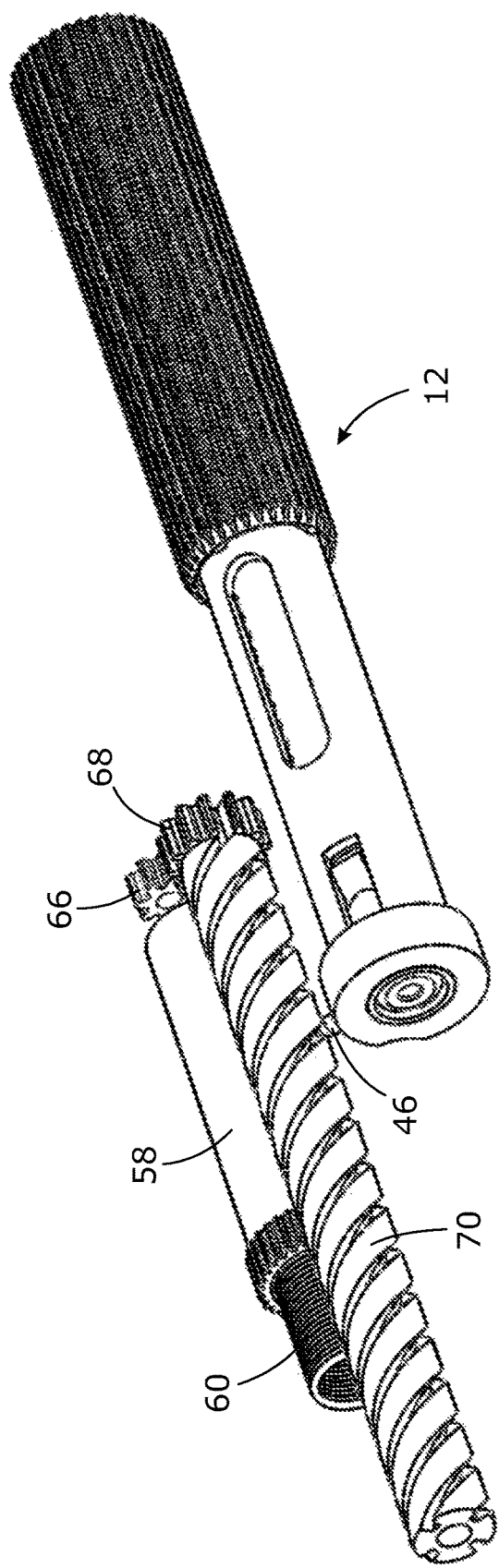
Figure 7D:
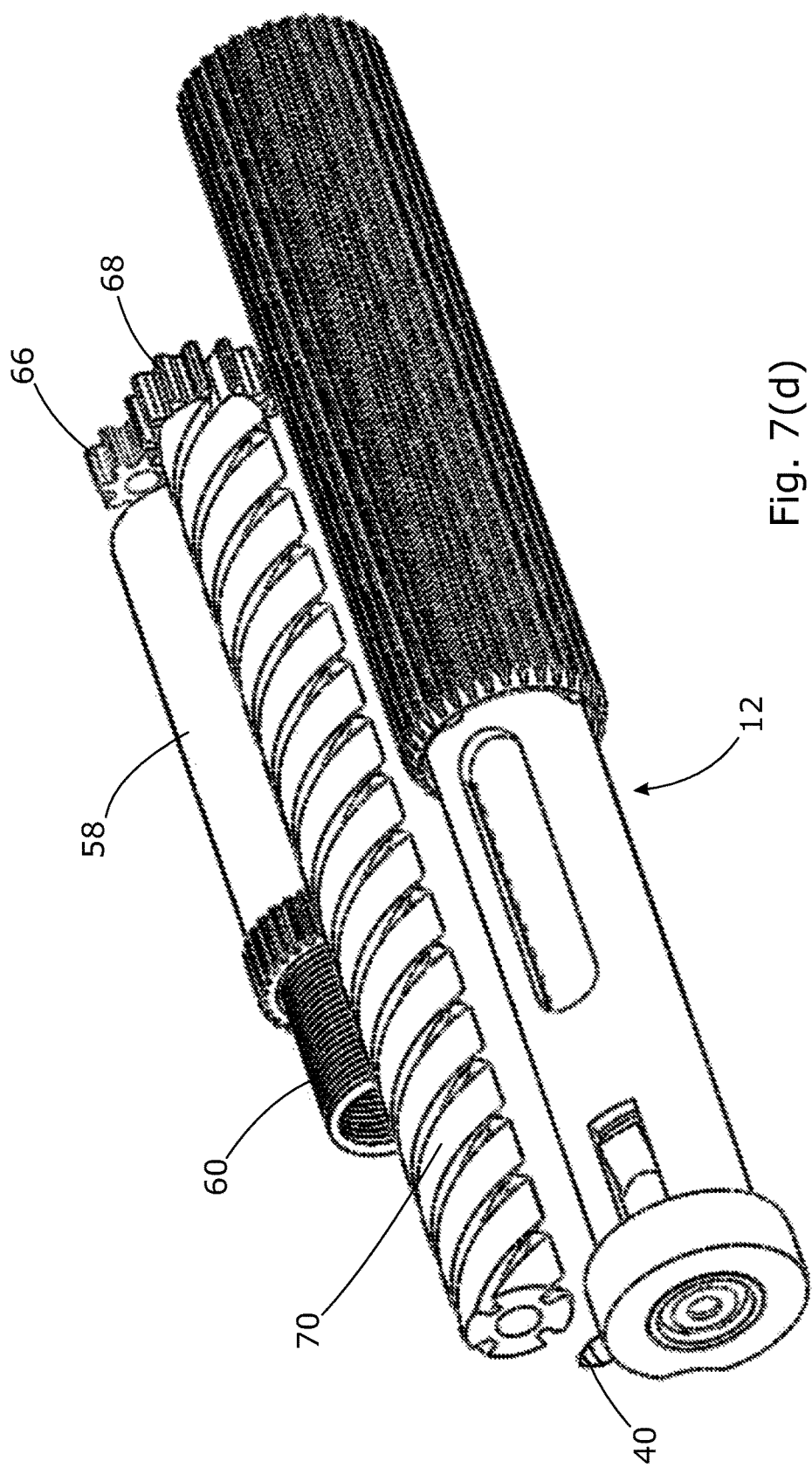

Referring now more particularly to FIGS. 4, 5 and 6, the transmission coupling that is effective upon insertion of the syringe assembly into the main housing of the autoinjector to prime the drive mechanism, will now be described. Within the housing 56 is rotatably mounted a hollow cylindrical drive shaft 58 inside which is anchored one end of a torsion spring 60, the other end of the torsion spring being anchored to a fixed part of the housing (not shown). At its rear end, as is seen more clearly in FIG. 6 the hollow drive shaft 58 has an integral input toothed gear portion 62 and at its forward end portion the hollow drive shaft has an output toothed gear portion 64; both the input and output gear portions are rotatably fixed with respect to the drive shaft 58. An input idler gear 66 meshes with the input gear 62 with the idler gear then itself meshing with a toothed gear 68 integral with the rear end of a screw shaft 70 having a 4-start thread extending along its length, the screw shaft being rotationally mounted within the housing 56. As can be seen in FIG. 6, the toothed gear 68 on the screw shaft is cut away at equi-spaced intervals as shown at 72 to allow access to the 4-start thread. The output gear 64 on the hollow drive shaft 58 meshes with an output ratcheted transfer gear 74 which resists unwinding movement of the drive shaft 58 as it is being charged, and so holding the energy of the torsion spring 60. During loading, as the syringe assembly moves from the position shown in FIG. 5 to that of FIG. 4, the splined outer surface of the plunger 52 slides past the ratcheted output transfer gear 74 and meshes with it shortly after charging of the mechanism is complete, and the ratcheted output transfer gear 74 has stopped rotating. The forward outside end of the plunger 52 is chamfered to ensure that the longitudinal meshing proceeds smoothly.

Turning now to FIGS. 7 (a) to (d), the input transmission train that converts linear movement of the syringe assembly as it is inserted into the housing 56 into rotary motion is made when the drive peg 46 on the syringe carrier 38 slides through a gap defined by one of the cutaway regions 72 to enter one of the threads 76 of the screw 70. As loading occurs, the syringe carrier 38 is prevented from rotating within the housing as the peg is constrained to move along a longitudinal slot in a sleeve 78 which slideably receives the syringe assembly as it is loaded (see FIG. 8). As the drive peg 46 moves along the screw it causes the screw 70 to rotate and this rotation is transferred via toothed elements 68, 66 and 62 to the hollow drive shaft which is rotated against the bias of the torsion spring 60 (FIGS. 7(b) and 7(c)). This also causes rotation of the ratcheted output transfer gear 74 which during this period is not in mesh with splined surface of the plunger 52 as the latter is axially displaced therefrom. Shortly before the syringe assembly 12 is fully home in the housing 56, the drive peg 46 exits the relevant thread 60, 76 and moves forwardly beyond the end of the screw, but the torsion in the torsion spring 60 is held by the ratcheted output transfer gear 74 (see FIGS. 11(a) and (b)).

Referring to FIG. 8, the sleeve 78 which slideably receives the syringe assembly 12 is shown. The sleeve is of cylindrical form, and has a slot 80 which extends down one side of the cylinder. At its rear end (not shown) the slot widens just short of the end of the sleeve to provide a tapered inlet guide for the drive peg 46. At the front end of the sleeve 78 a further short slot is formed to leave a resilient finger 82 with a barb 84 with a radial forward surface and an inclined rear ramp surface.

Figure 9:
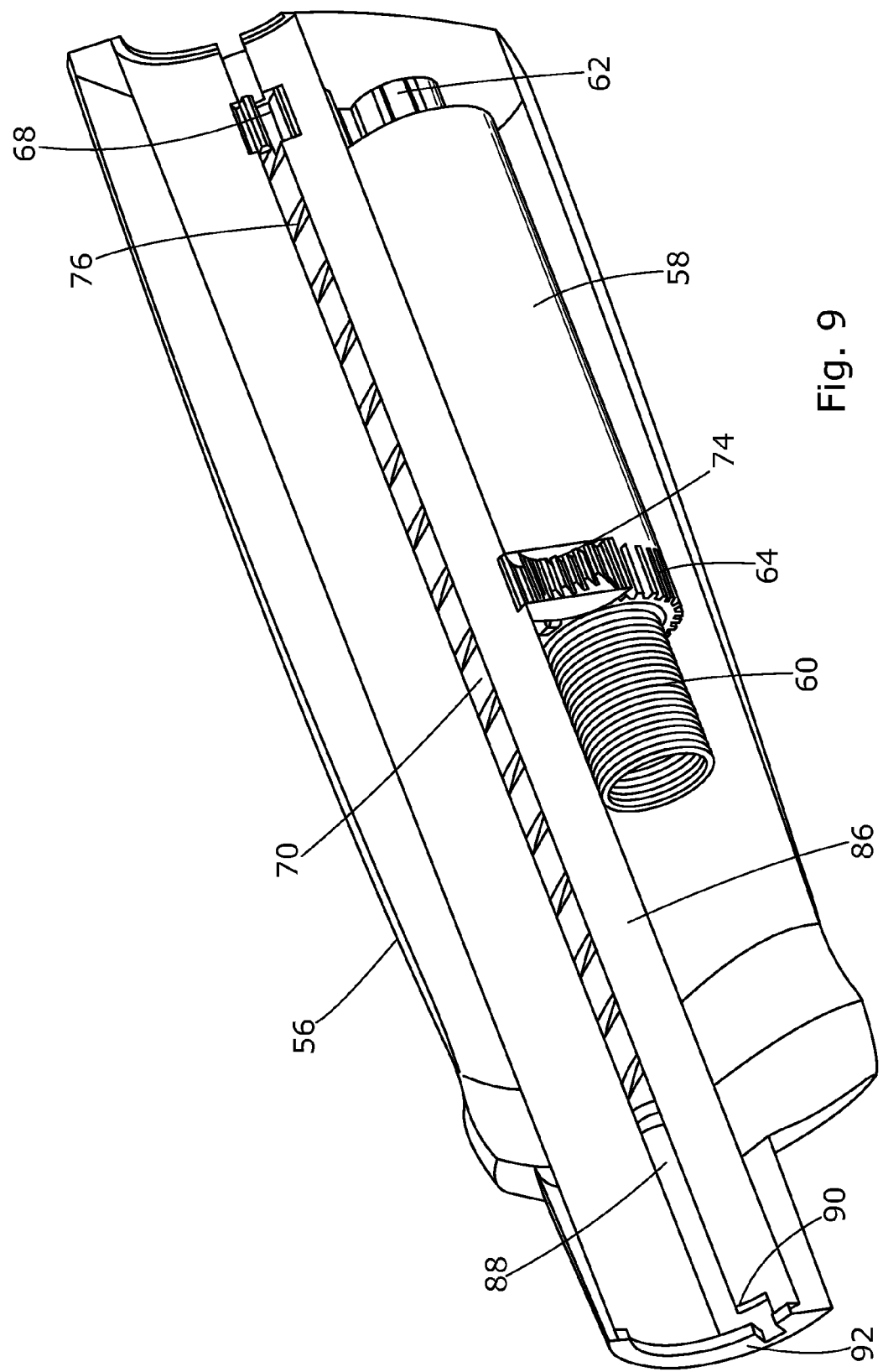
FIG. 9 is a perspective, section view taken on lines IX-IX of FIG. 4 to show a detail of the slot and keyway arrangement in the housing.
Figure 10A:
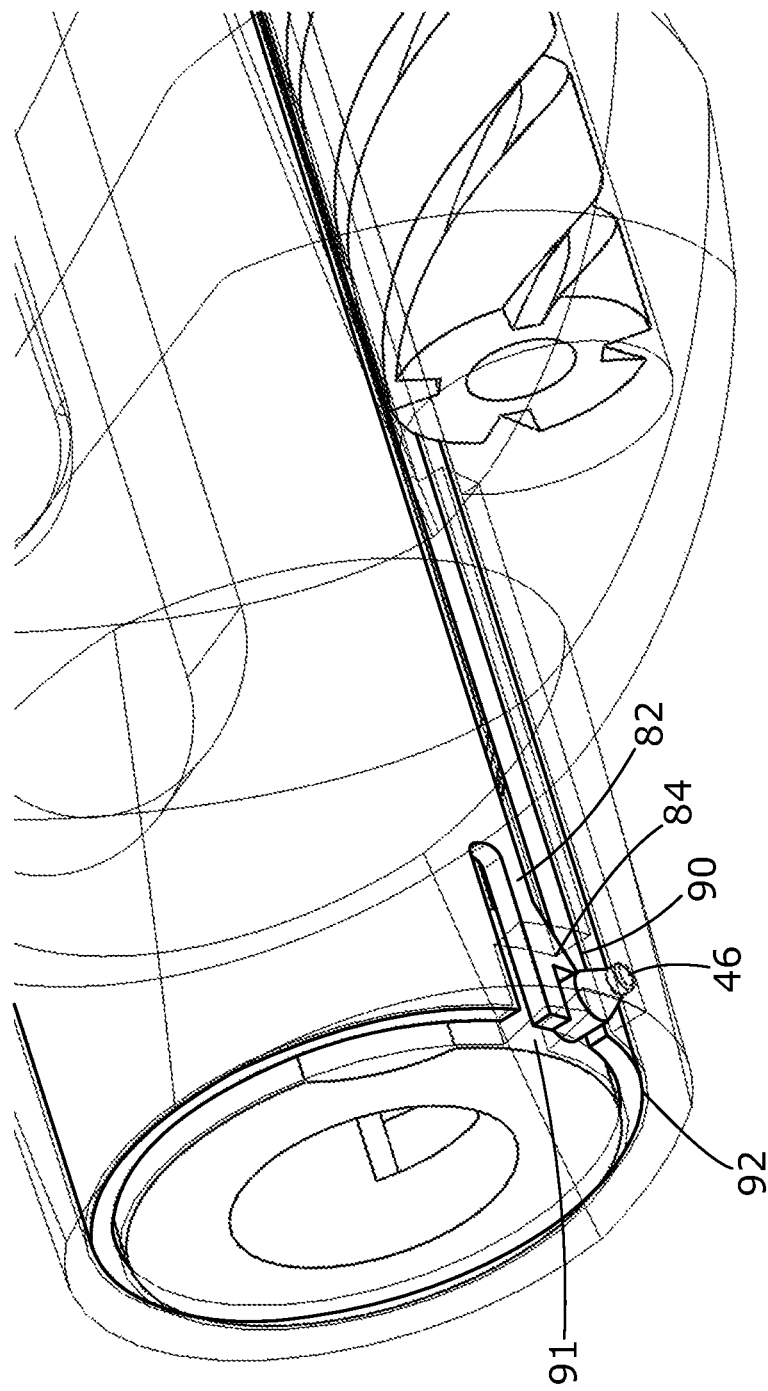
FIGS. 10($a$) and ($b$) are detailed views showing the retention arrangement for retaining the syringe assembly in the autoinjector.
Figure 10B:
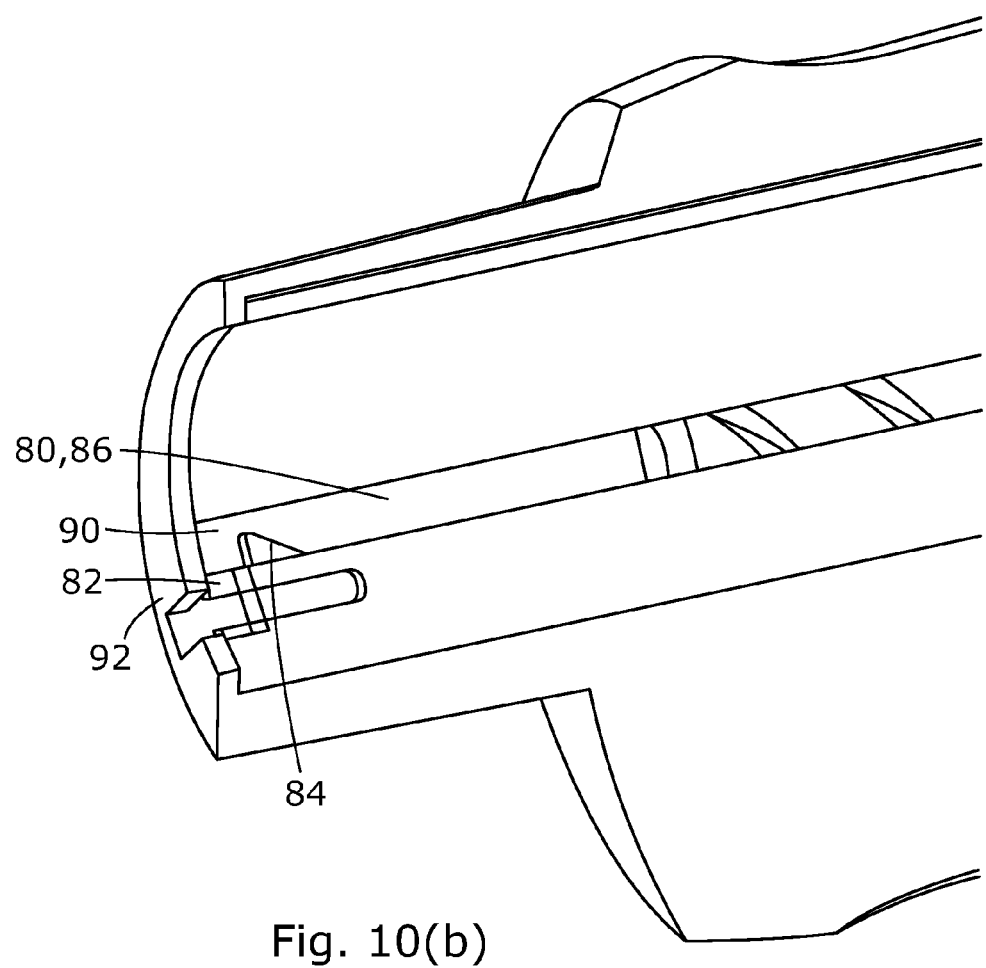
Figure 11A:
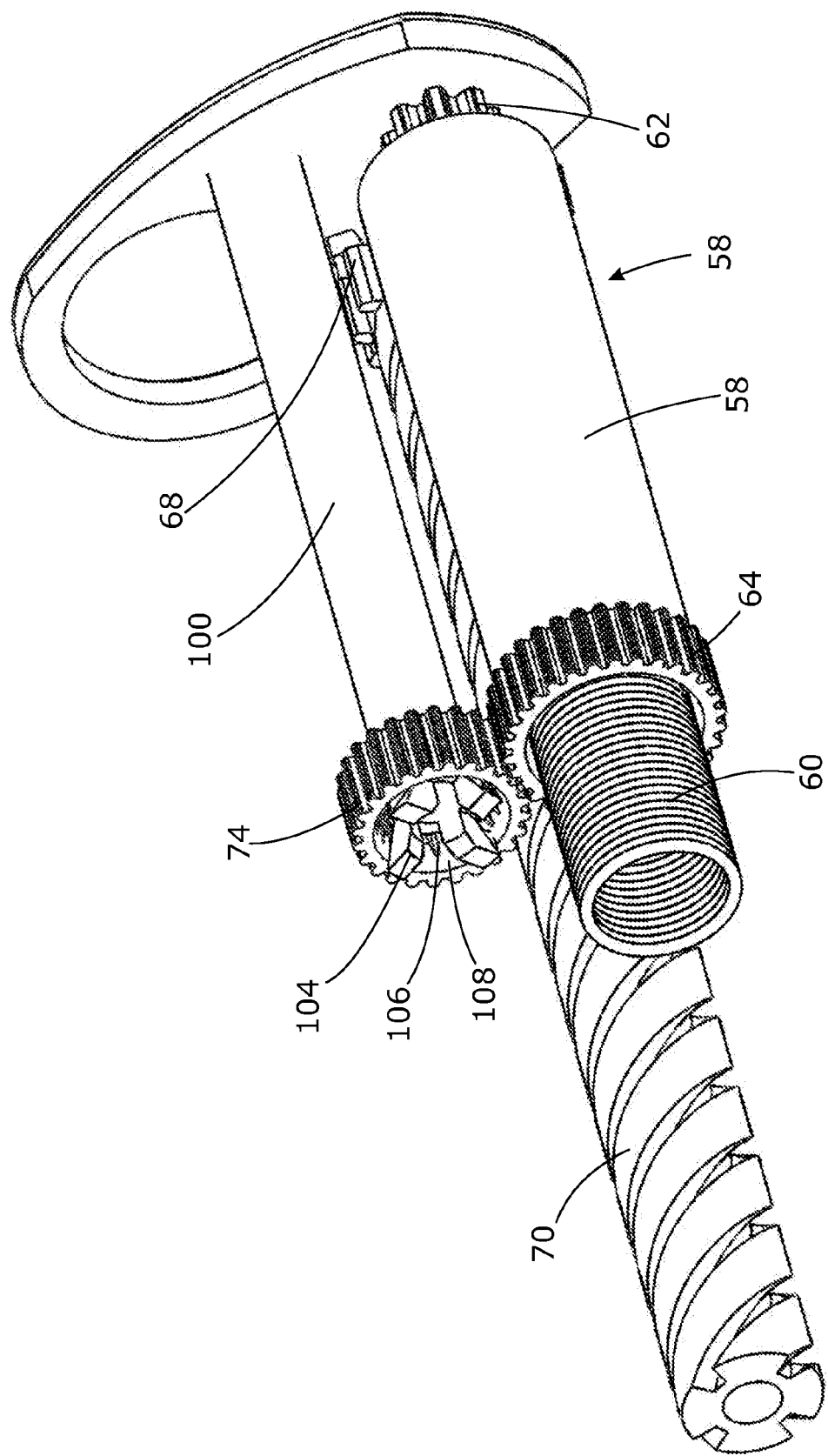
FIGS. 11($a$) and 11($b$) are detailed views on the firing button and associated mechanism.
Figure 12:
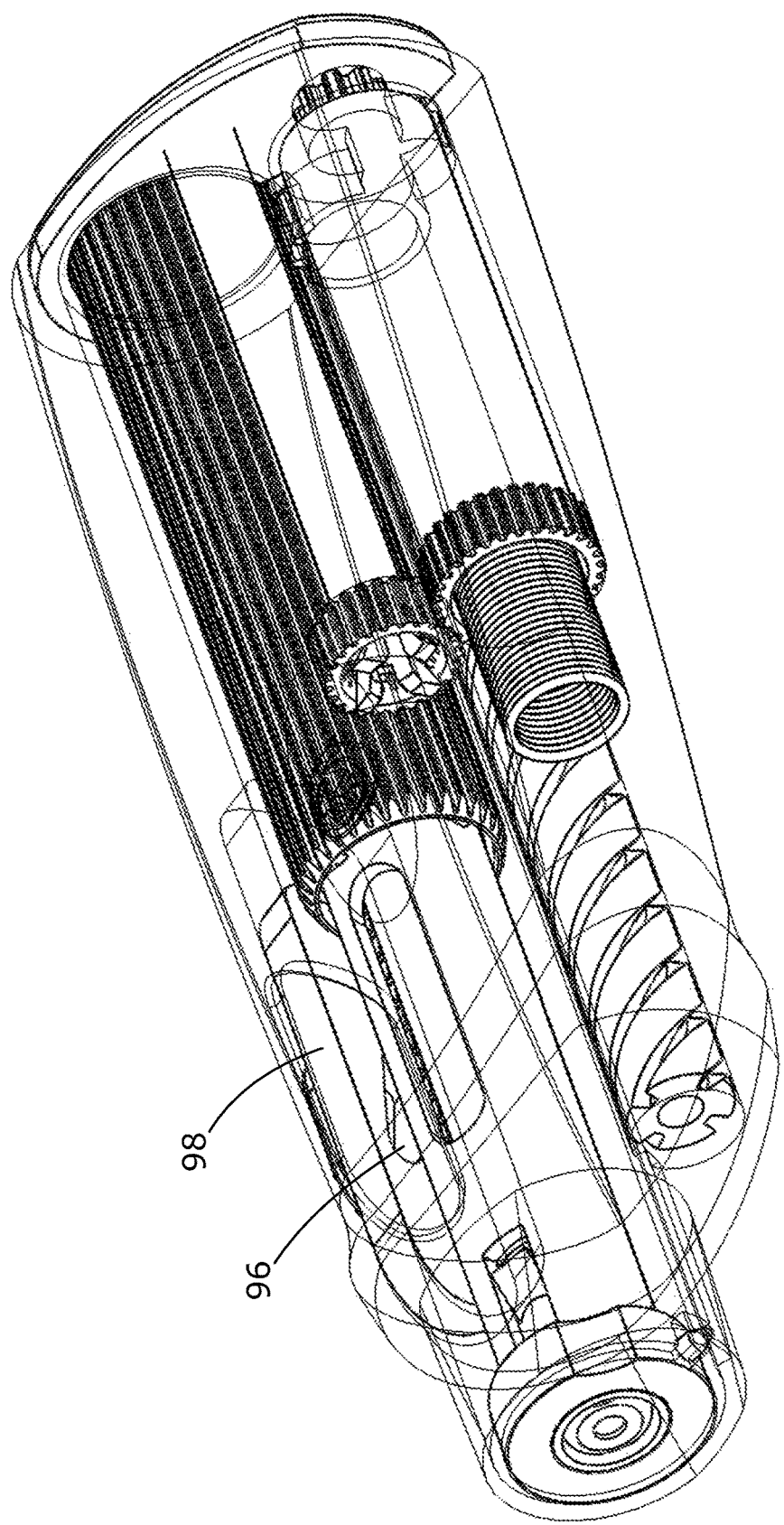
FIG. 12 is a view of the first embodiment of autoinjector device primed prior to an injection.
Figure 13A:
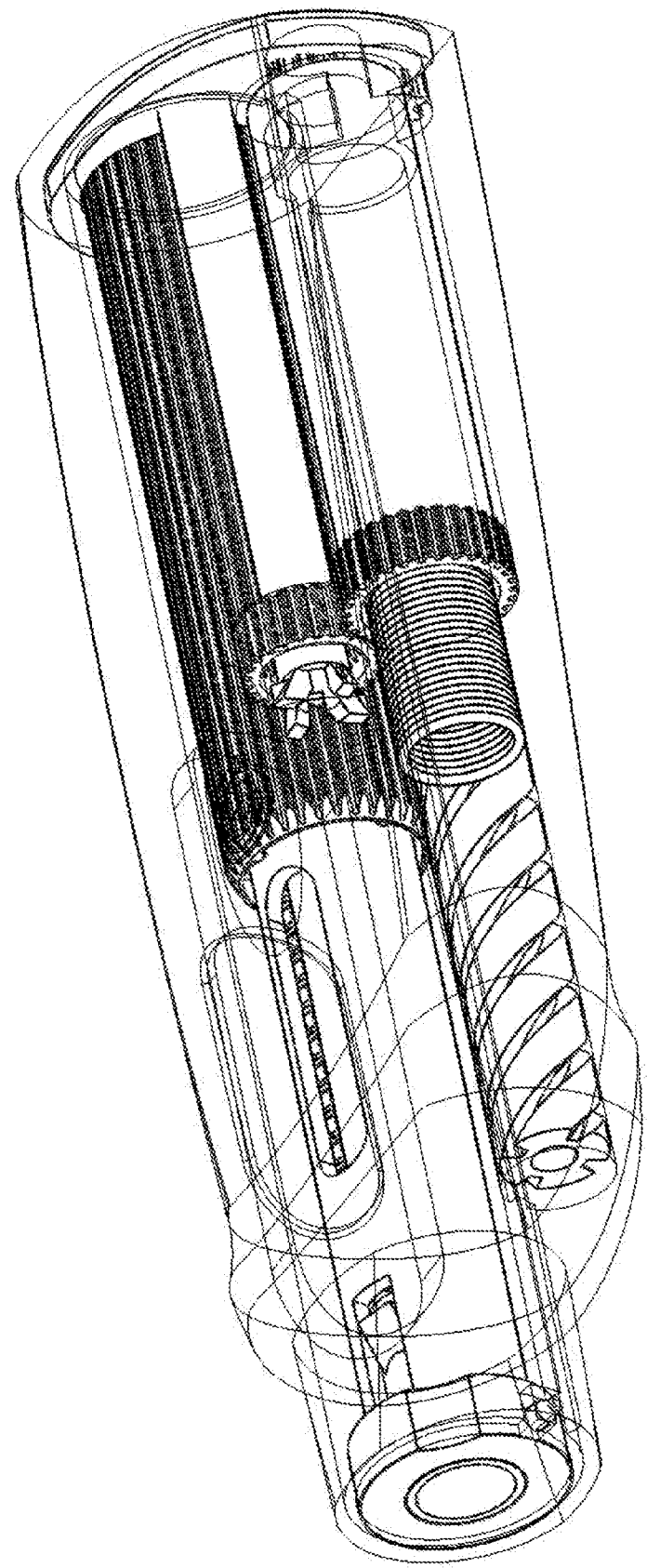
FIGS. 13($a$) to ($d$) show successive stages from firing through to complete delivery of medicament.
Figure 13B:
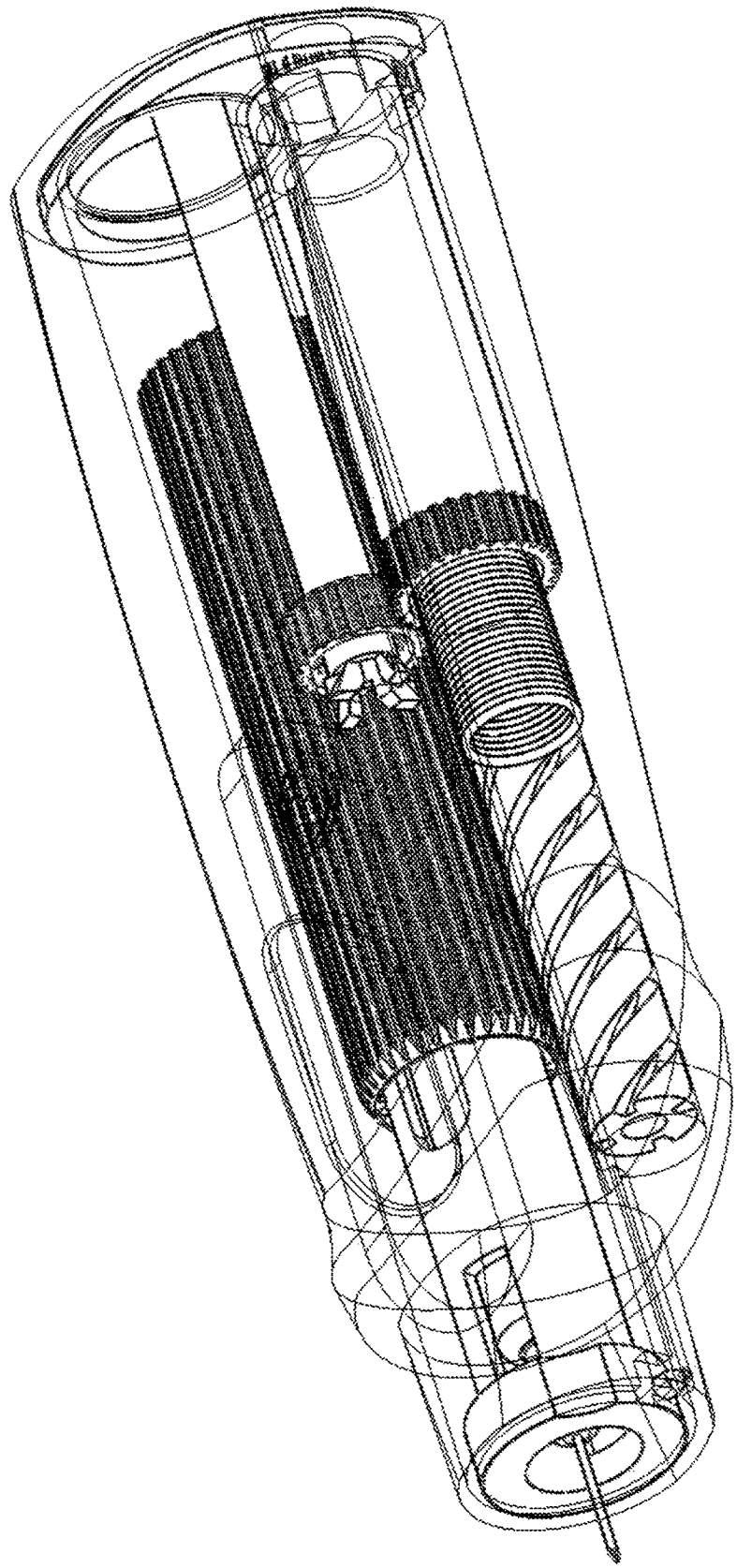
Figure 13C:
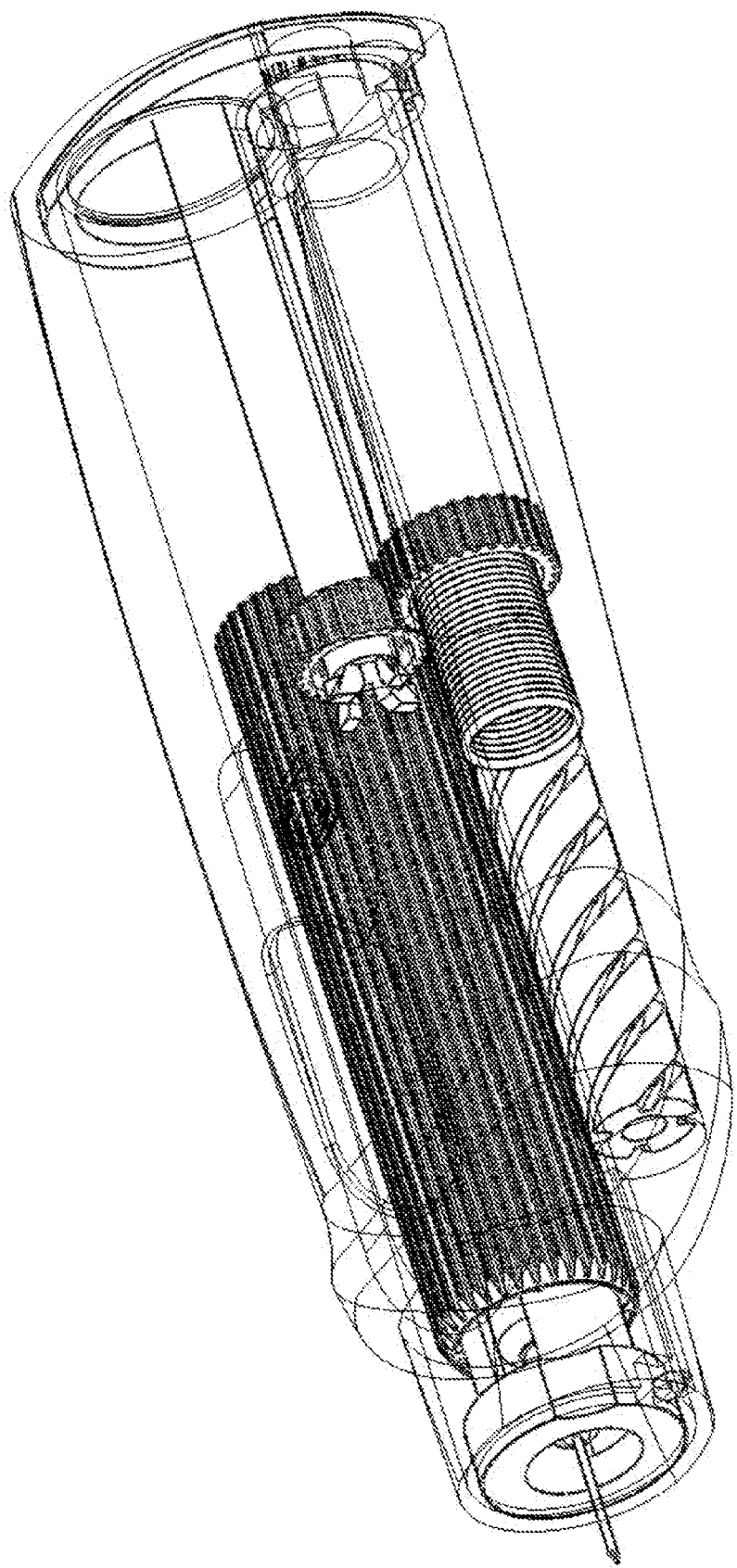
Figure 13D:
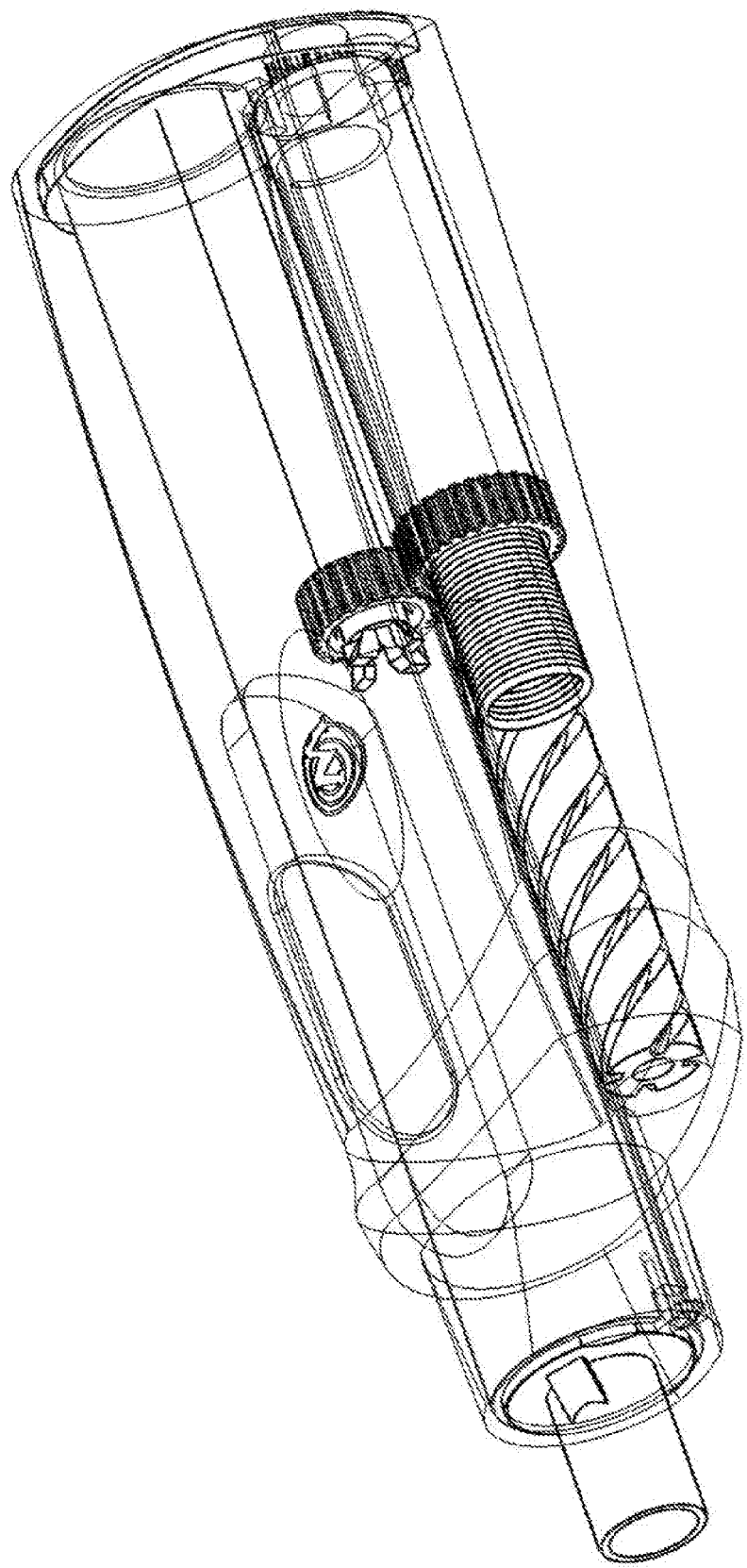
Figure 14A:
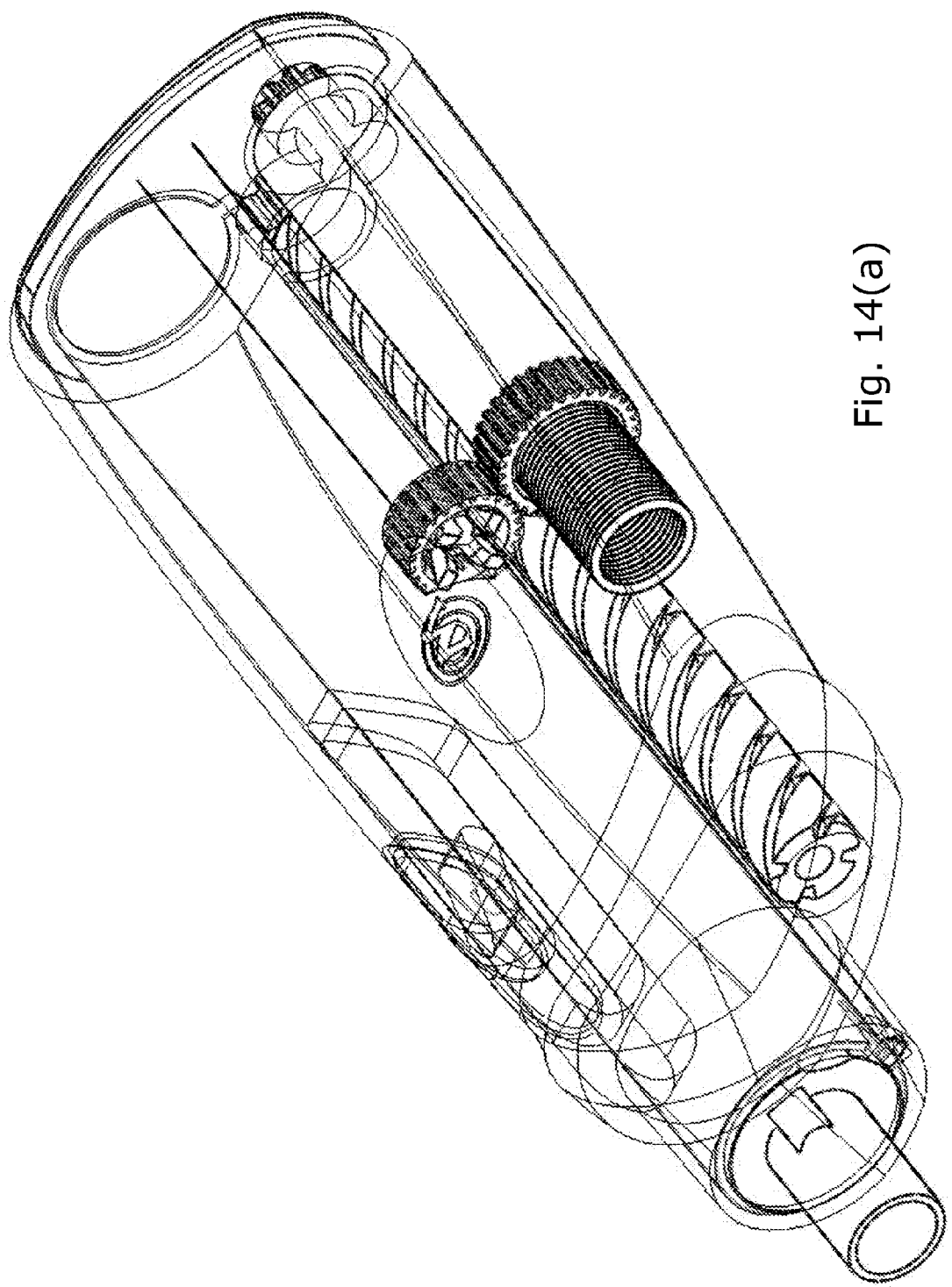
FIGS. 14($a$) to ($d$) are successive views showing ejection of the syringe assembly after use.
Figure 14B:
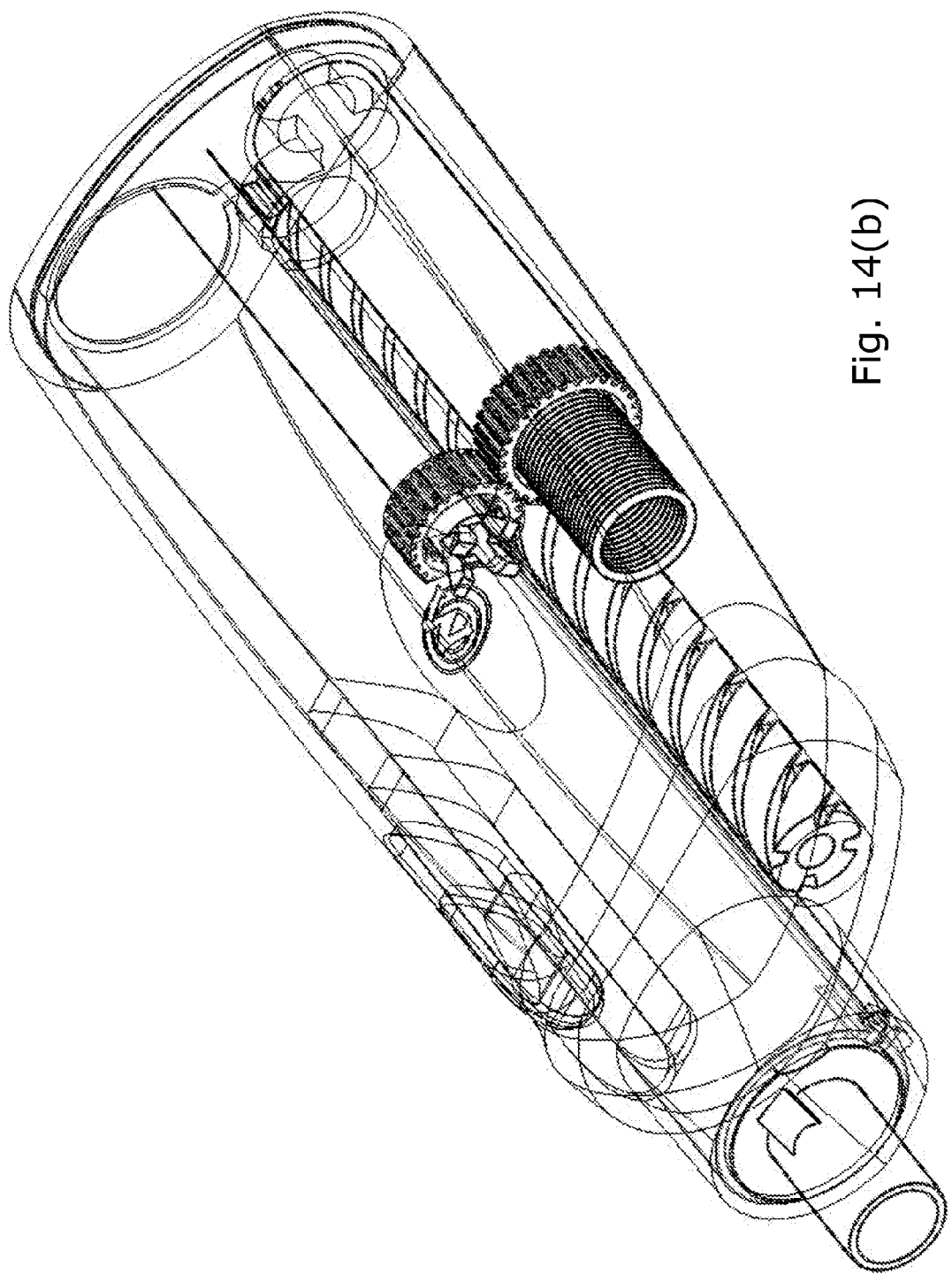
Figure 14C:
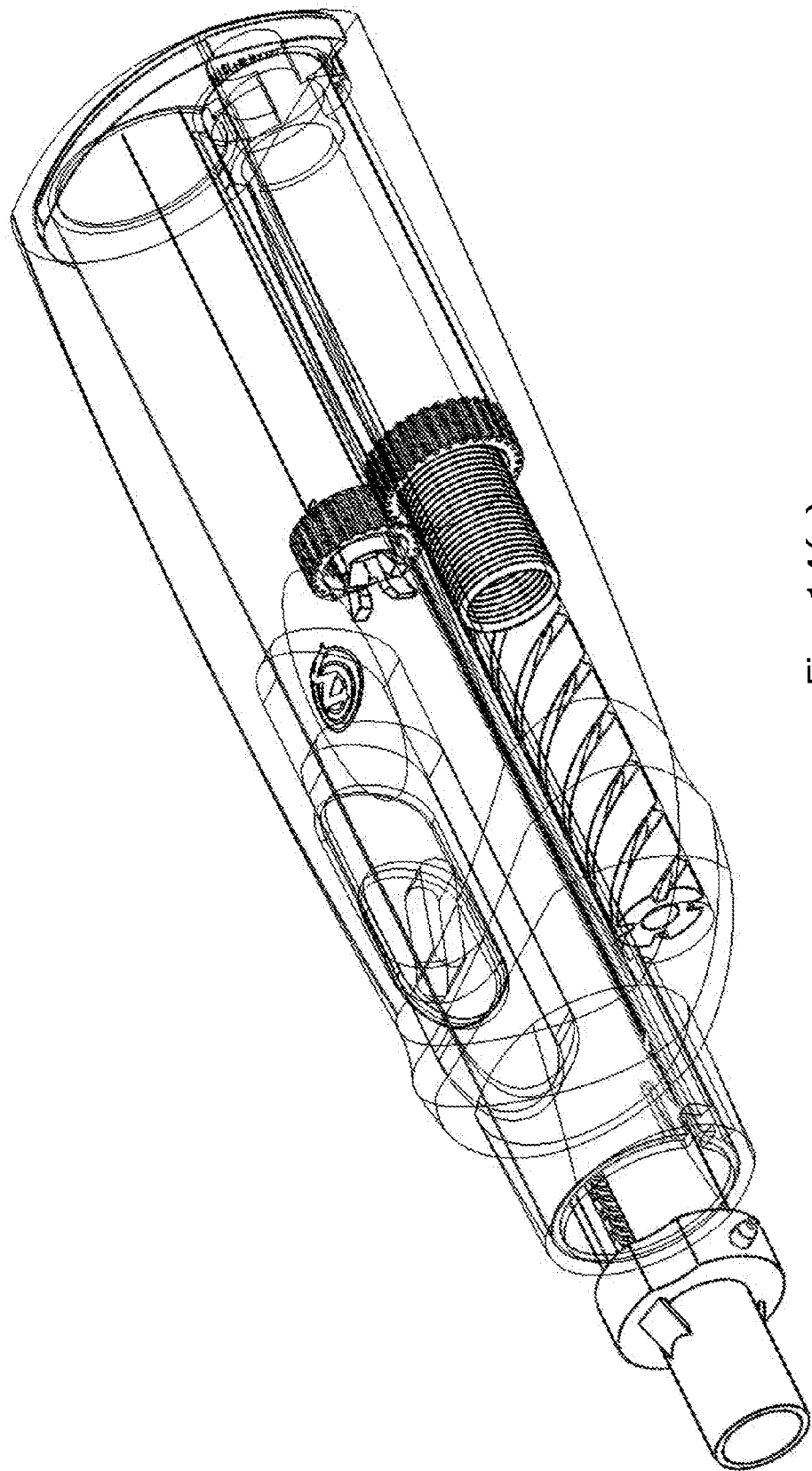

Referring now to FIGS. 9 and 10, the housing 56 has an internal wall 86 which has a slot 88 extending along its length which aligns with the slot 80 in the sleeve 78 and through which the drive peg 46 passes to engage one of the threads 76 in the drive screw 70. As seen in FIG. 9, the slot 88 is open at its rear end to allow introduction of the drive peg 46. At its front end, the slot 80 is cranked at 90 so that the slot exit from the housing is offset from the slot inlet. This means that on linear loading movement of the syringe assembly, the drive peg 46 passes down the full length of the slot to abut the end wall of the housing. In order to remove the syringe assembly forwardly, the assembly needs to be rotated slightly to navigate the drive peg 46 around the cranked portion. As seen in FIGS. 10(*a*) and (*b*), as the drive peg 46 nears its forwardmost position during loading, it snaps past the barb 84 on the resilient finger 82 of the sleeve 78, thus trapping the syringe carrier 38 against longitudinal movement for the duration of the injection. The sleeve 78 has a projecting lug 94 (see FIG. 8) which is received in an inclined recess 96 on a forwardly slideable eject button 98 (see FIG. 12). Sliding the eject button 98 stage rotates the syringe assembly so that the drive peg 46 is aligned with the slot exit 91 in the end wall 92 allowing the syringe assembly to be ejected forwardly.

Referring now to FIGS. 11(*a*) and (*b*), as noted previously, during priming, the output gear 64 on the hollow drive shaft 58 drives a ratcheted output transfer gear 74. The gear 74 is rotatably mounted on a firing rod 100 which is connected to a firing button 102 which projects slightly beyond the end of the housing and which is spring biased rearwardly. As seen in more detail in FIG. 11(*b*), the front end of the firing rod 100 is provided with four outwardly splayed resiliently deformable ratchet claws 104. The inner surface of the transfer gear 74 is splined 106 and the inner forward end chamfered at 108. In use, when the components are in the relative position shown in FIG. 11(*a*), the ratchet claws are in engagement with the splines 106 on the inside of the transfer gear 74 and exert a uni-directional ratchet action to allow the hollow drive shaft 58 to rotate in the charging direction to charge the torsion spring 60 as the syringe assembly is introduced into the housing, but to hold the drive shaft 58 against movement in the discharging direction once the drive peg 46 is no longer in engagement with the screw 70.

As seen in FIG. 11(*b*), when the firing button is pushed forwardly, shifting the ratchet claws 104 out of engagement with the splines 108, the constraint on movement of the gear 74 and the output shaft 58 is removed so that the two can rotate as driven by the torsion spring 60. It will be recalled that the transfer gear 74 is meshed with the outer spline surface of the plunger 52 thereby transferring rotary motion to the plunger. At a position intermediate that shown in FIGS. 11(*a*) and (*b*), the claws 104 provide a braking effect, so allowing the user to modulate the output speed of the drive mechanism and thereby the speed and cycle time of the injection process.

Figure 1:
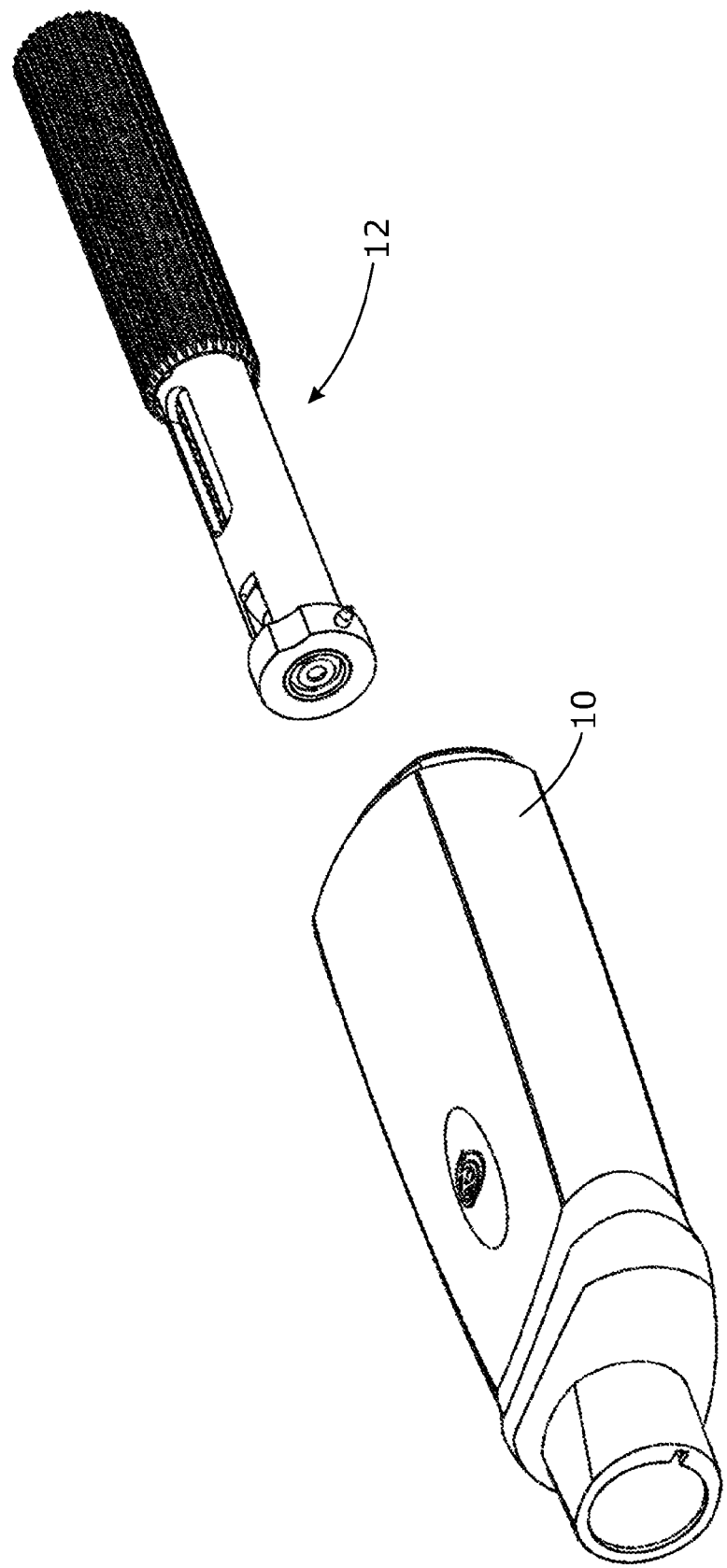
FIG. 1 is a general perspective view of a first embodiment of autoinjector in accordance with this invention, prior to loading of the syringe assembly.

In use, a disposable syringe assembly is offered up to the rear of the drive unit 10 as shown in FIG. 1. The flange 40 enters the sleeve 78 with the drive peg 46 projecting through the aligned slots 80 and 88. The drive peg 46 engages the screw 70. The drive peg 46, the thread 76 in the screw, and the tooth gear 68 on the screw, the idler gear 66 and the integral input gear 62 on the drive shaft 58 acting as an input transmission train which converts the linear movement of the syringe assembly 12 into a rotary movement which charges the torsion spring 60 against the ratchet action of the transfer gear 74. Shortly after the drive peg 46 exits the end of the screw 70, the external splines on the plunger 52 engage the output transfer gear 74, and thereafter the drive peg 46 snaps past the barb 84 to hold the syringe carrier against longitudinal movement.

Having removed the rigid needle shield 22 by suitable means, the charged autoinjector is held up to the injection site and, when the user is ready, they press the firing button which releases the output transfer gear 74 for rotation so that the mechanical energy in the torsion spring 60 is transmitted by an output transmission coupling comprising the gear 64, the output transfer gear 74 and the splines on the plunger 52 to rotate the plunger 52 so that it moves forwardly relative to the syringe carrier. FIG. 13(*b*) shows the device after the plunger has moved about half way down the syringe carrier. The drive rod 54 of the plunger moves the syringe forwardly against the rearward bias applied by the connecting spring portions on the needle shield 26 to cause the needle 20 to penetrate the injection site. Forward movement of the syringe is arrested when the springs bottom out whereupon continued forward movement of the drive rod moves the syringe piston 18 forwardly to express a dose. During this phase, as noted above, the user may moderate the speed of operation by removing or reducing pressure on the firing button. Once the injection is complete (FIG. 13(*c*)), the user removes the device from the injection site and the forward part of the syringe shield 26 may now move forwardly to shroud the needle with the barbs 36 snapping out against the end face of the flange to lock the shroud in its shielding position (FIG. 13(*d*)).

In order to eject the spent syringe assembly the eject button 98 is pushed forwardly, which rotates the syringe assembly anti-clockwise as viewed from the front so that the drive peg 46 is aligned with the slot in the end wall 92 so that the assembly can be removed by pulling on the shield.

Referring now to the second embodiment shown in FIGS. 15 to 20, this embodiment comprises a reusable drive unit 110 into which is located longitudinally a syringe assembly 112, but in this embodiment the syringe assembly is loaded rearwardly through the front end face of the housing. As in the previous embodiment, the drive unit 110 contains a spring-driven mechanism for providing drive for operation of the autoinjector. The drive mechanism is mechanically charged by harnessing and converting the linear motion as the syringe assembly is pushed home into the drive unit to wind up the drive mechanism.

Figure 17:
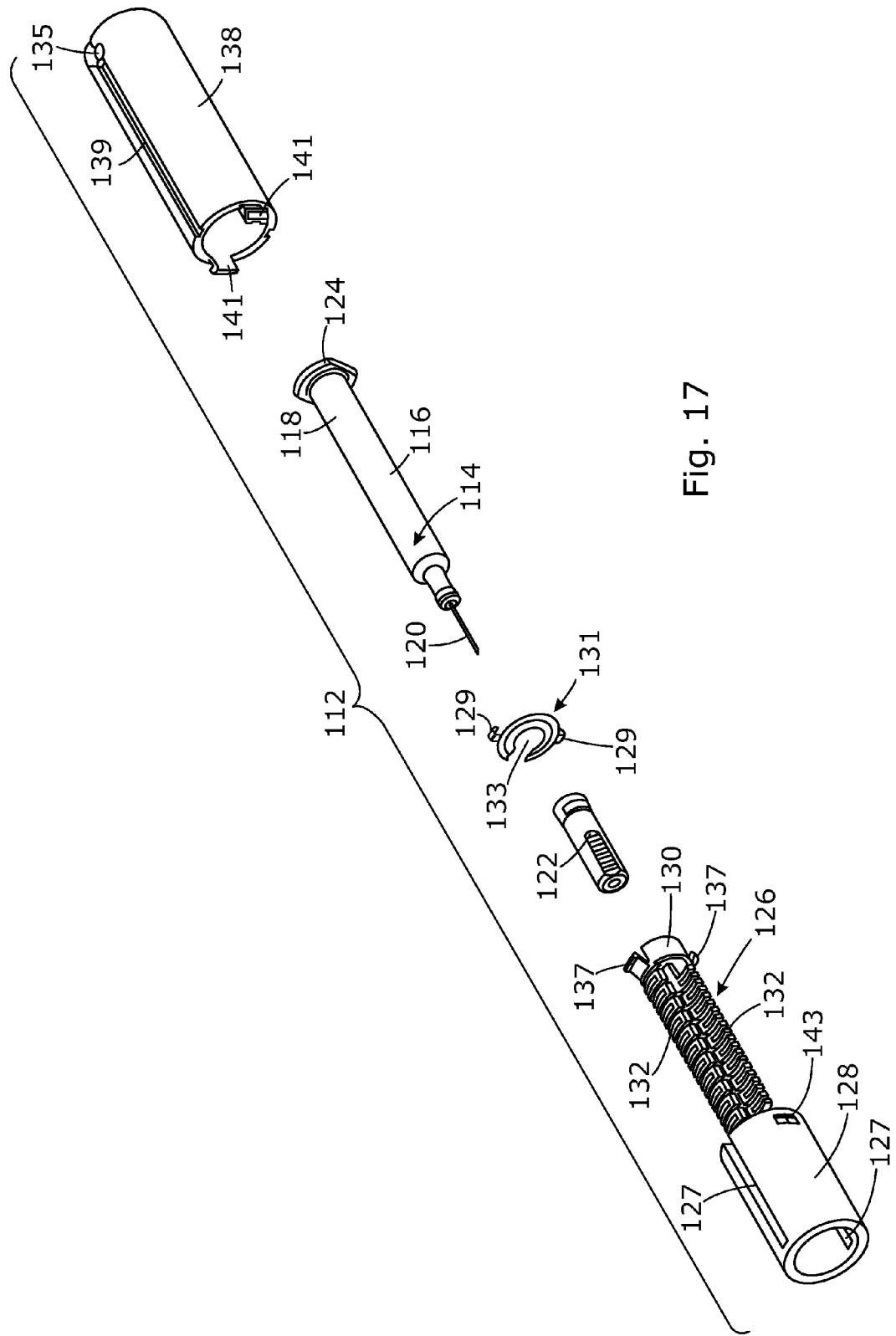
FIG. 17 is an exploded view of the syringe assembly for use in the second embodiment.

Referring now to FIG. 17, the syringe assembly includes a syringe 114 having a syringe body 116 containing a piston 118 slideably mounted within the body of the syringe to expel a dose through a needle 120. Prior to use, the needle 120 is covered by a rigid needle shield 122. At its rear end the syringe carries a syringe flange 124. The syringe 114 is concentrically received within a generally tubular syringe shield 126 having a forward shielding portion 128 and a rearward collar 130 which abuts the flange 124 of the syringe 114. The forward and rearward parts 128, 130 are connected by an integrally moulded pair of spring portions 132. The shielding portion 128 has opposed diametric slots 127 which slideably receive opposed diametric formations 129 of a pressed steel rigid shield remover 131 which is of generally disk form but having a keyhole recess 133 provided therein. In its initial condition, the rigid shield remover 131 is sandwiched between the rigid shield 122 and the forward facing shoulder at the change in diameter of the syringe body. The recess 133 is dimensioned so that it can slip over the reduced diameter section of the syringe body during assembly and is of smaller diameter than the rigid needle shield 122.

In the condition as supplied (i.e. with the spring portions 132 fully extended), the relative positions of the syringe 114 and the rigid shield remover 131 relative to the syringe shield 126 are such that the formations 129 sit in the rear ends of the slots 127. The syringe 114 is carried and located radially by the rearward collar 130 and the spring portions 132 of the syringe shield 126. A syringe housing 138 is snap fitted to the shielding portion 128 of the syringe shield 126, by means of teeth 141 on the housing snapping into recesses 143 on the shielding portion. The housing 138 and the shielding portion together define a generally cylindrical enclosure for the syringe in which the syringe can move longitudinally, biased rearwardly by the spring portions 132. The syringe is releasably latched in its rearmost position in the enclosure by outwardly directed barbs 137 on the rearward collar 130 of the syringe shield 126 latching into through recesses 135 at the rear end of the syringe housing 138. Twin external slots 139 run down the sides of the syringe housing 138, widening out at the recesses 135 and align with the slots 127 on the outside of the shielding portion 128.

Figure 15:
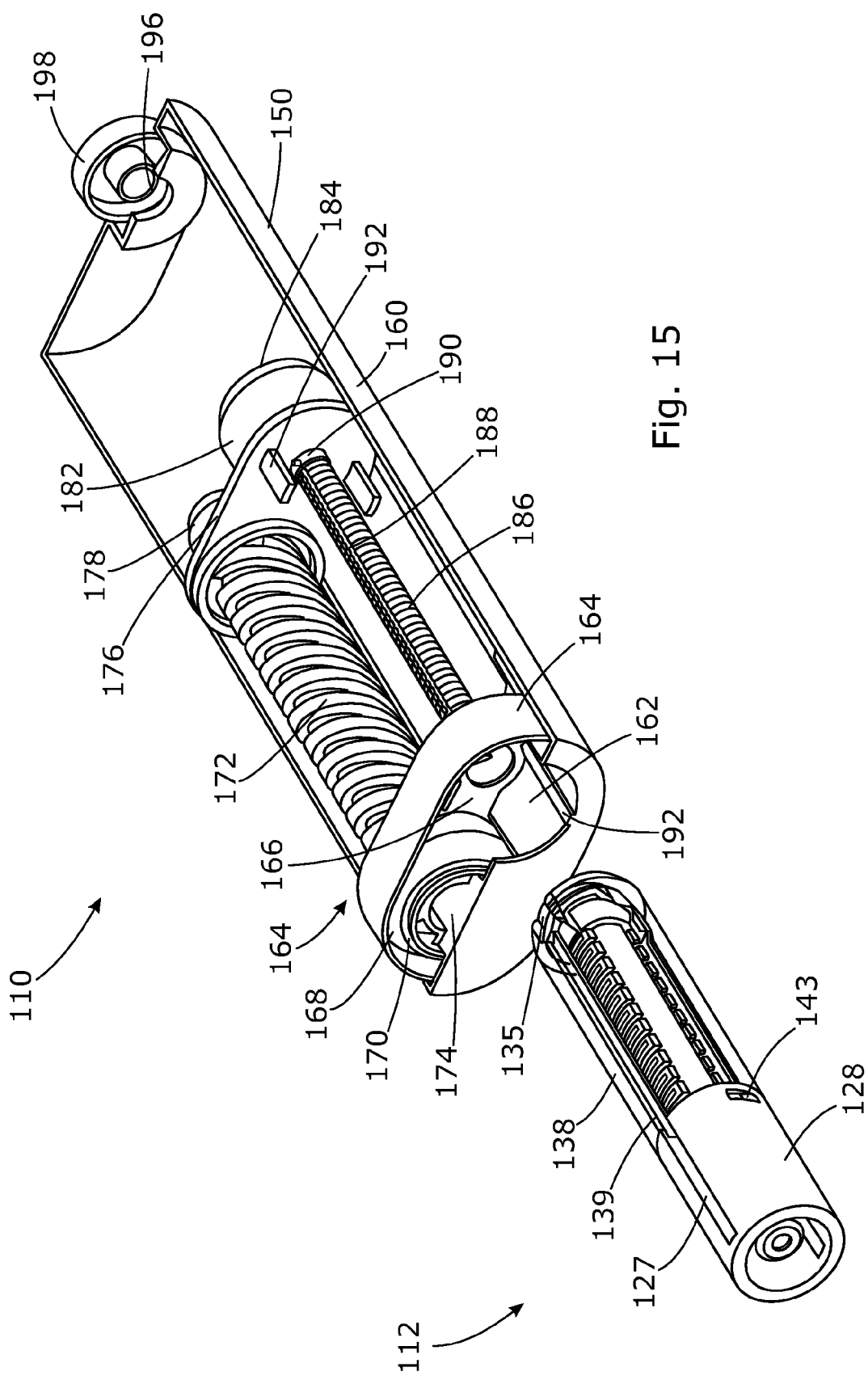
FIG. 15 is a general perspective view of a second embodiment of autoinjector in accordance with this invention, prior to loading of the syringe assembly and with the top part of the housing removed.
Figure 16:
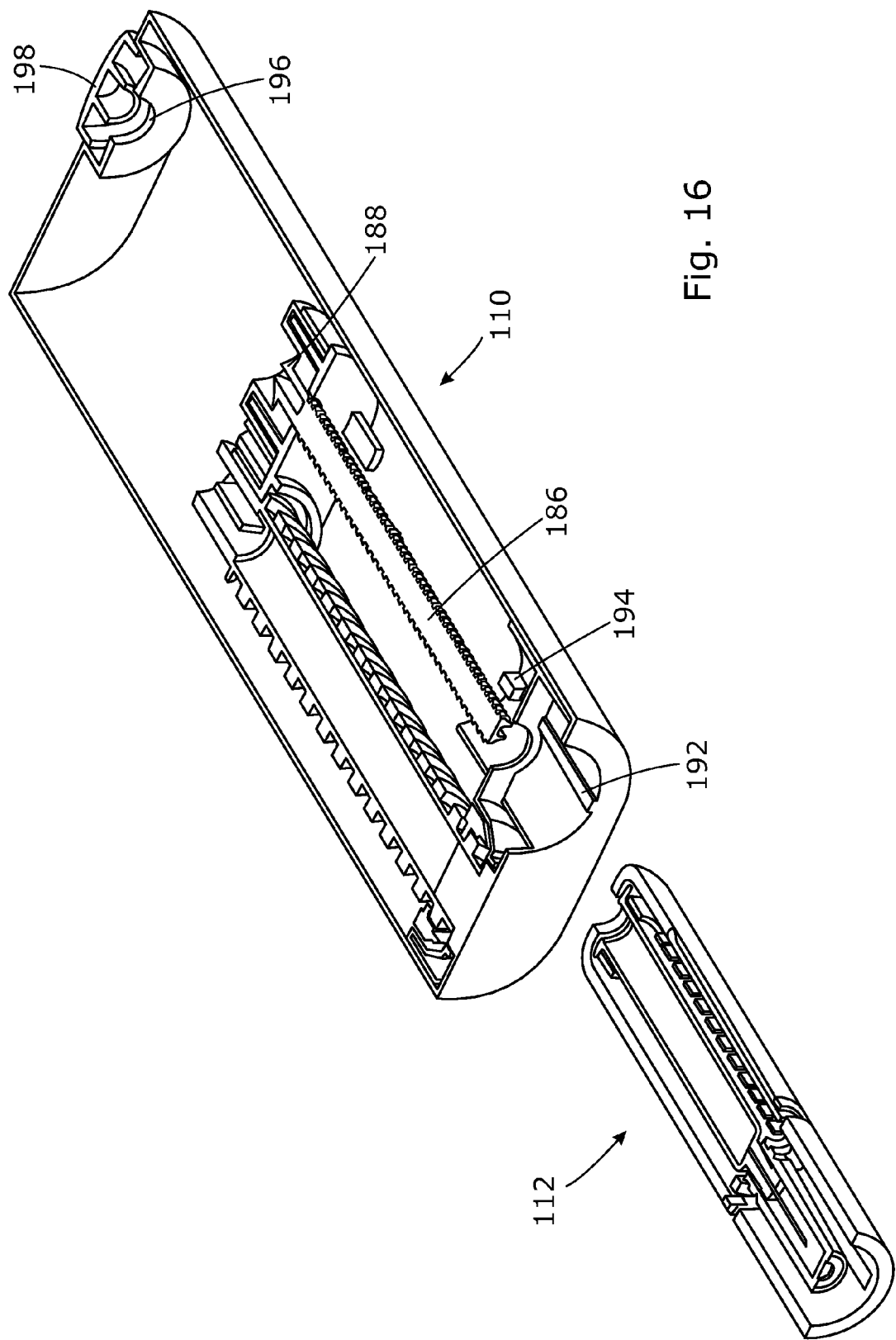
FIG. 16 is a horizontal section view through the arrangement of FIG. 15 in a pre-primed position.
Figure 18A:
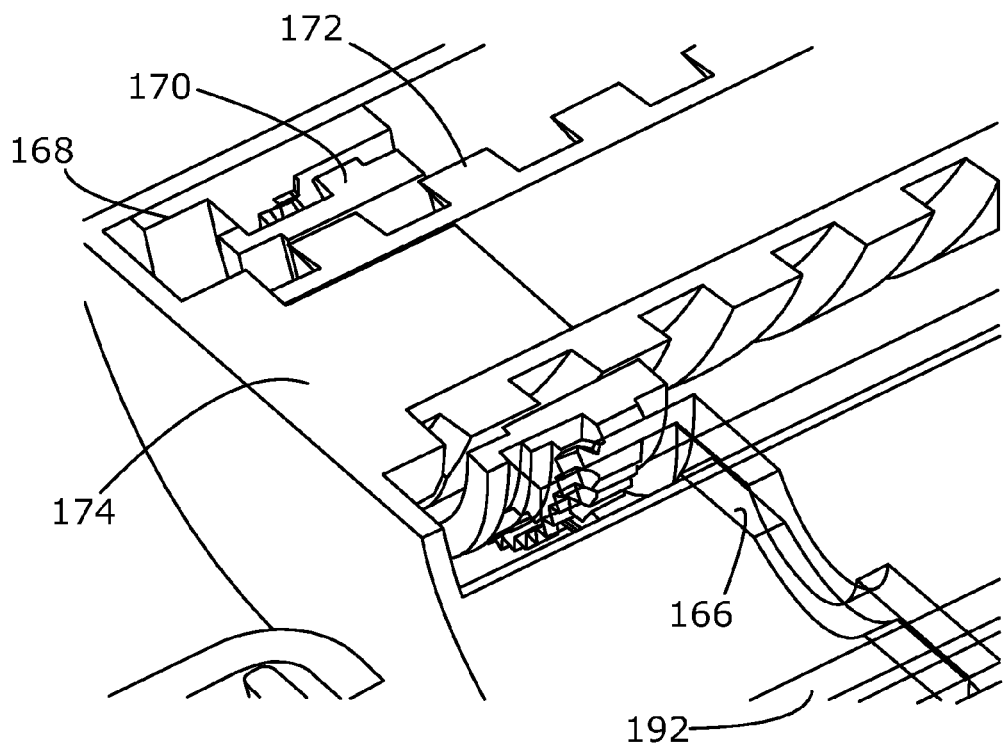
FIGS. 18($a$) and ($b$) are detailed views on the arrangement of FIG. 15 showing the arming plate and the slip disk in disengaged and engaged positions respectively at the start of a priming action.
Figure 18B:
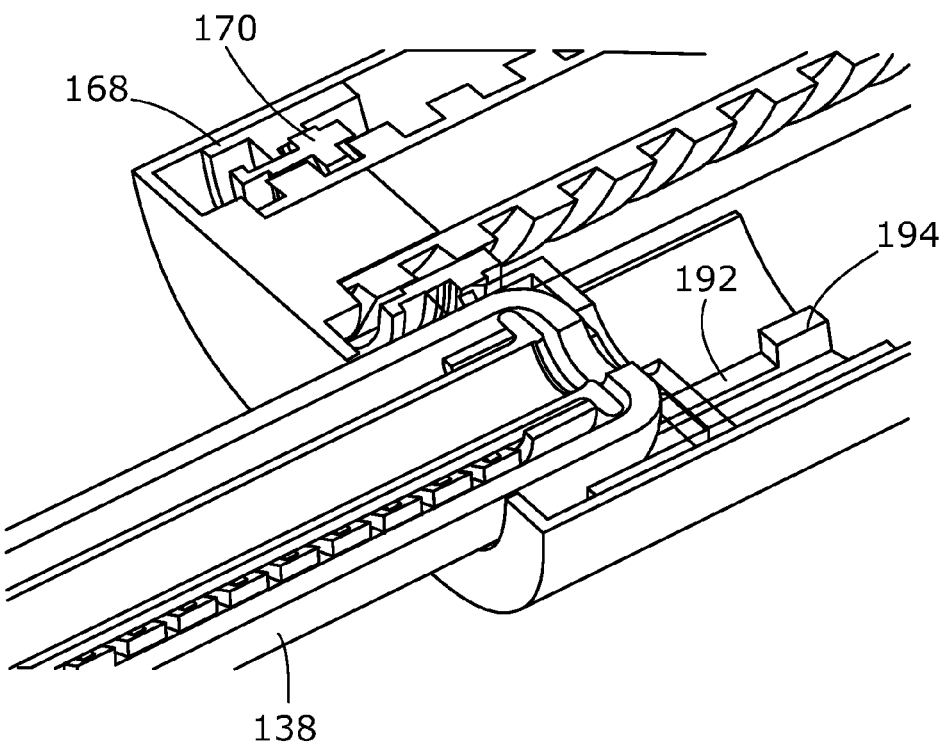

Turning now to the drive unit 110 and in particular to FIGS. 15 and 16, the drive unit 110 comprises a casing 150, the lower part only of which is shown in FIGS. 15 and 16. The housing defines an opening 162 at the front end into which a syringe assembly 112 may be inserted. Mounted for linear sliding movement in the housing against the bias of a return spring (not shown) is an arming plate 164 which includes a socket 166 for receiving the rear end of a syringe assembly and, at the other side thereof, a rearwardly facing cup 168 having an internal splined surface which engages the external splined surface of a slip disk 170. The slip disk 170 is threaded onto a hollow arming screw 172 which is mounted for rotation between a lug 174 projecting inwardly from the front wall of the housing, and a bore in a spring plate 176 mounted within the housing. The slip disk 170 is captive in the arming plate for limited longitudinal movement between a disengaged position in which it can rotate freely and an engaged position in which it is locked against rotation relative to the plate, as seen in FIGS. 18(a) and (b) respectively. A light spring (not shown) urges the slip disk away from the cup 168. The arming screw projects beyond the spring plate 176 to provide a projecting shaft portion 178 which is slotted at 180 to receive one end of a constant torque spring 182. The rear part of the screw 172 is relieved to leave a plain cylindrical surface 173 at the rear end facing the spring plate 176, to allow the slip disk 170 to disengage from the screw when the arming plate is in its rearmost position, and whilst the constant torque spring rewinds onto the shaft portion 178 once the device is fired.

Figure 19:
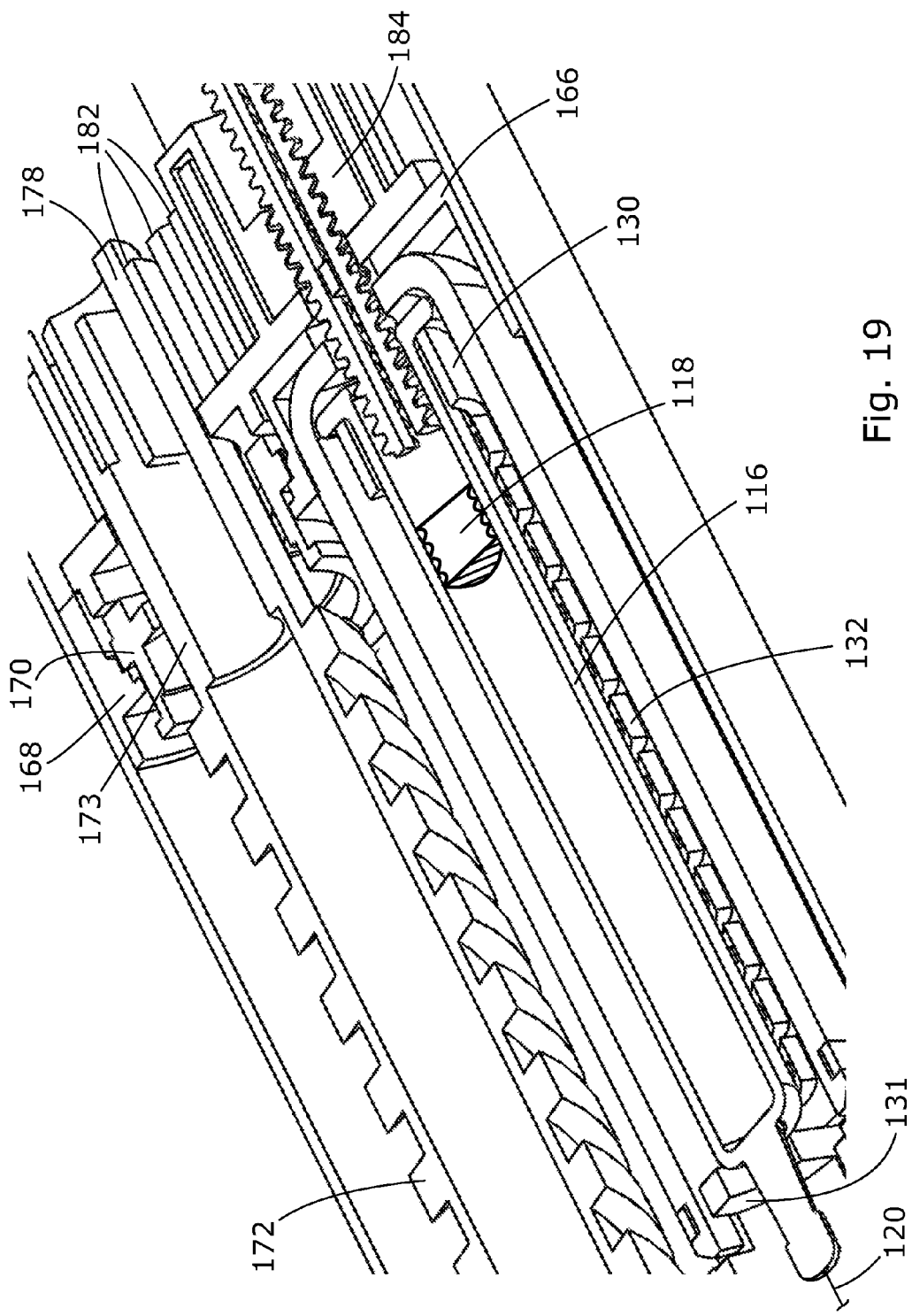
FIG. 19 is a detailed view of the slip disk and plain end of the screw disengaged on priming the device.
Figure 20:
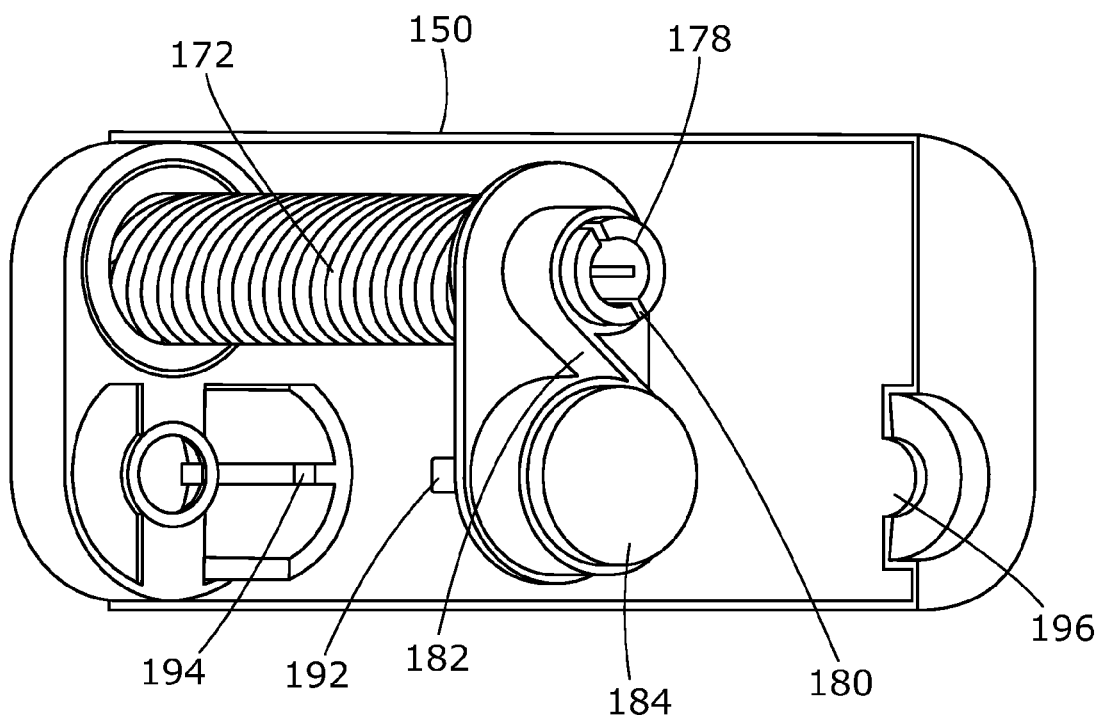
FIG. 20 is a perspective view on the rear end constant torque motor of the arrangement.

As seen in FIG. 19, the constant torque spring passes around the shaft 178 and then reverses its curvature to pass around a drive gear 184 which is rotatably mounted on the spring plate 176. The drive gear 184 is internally threaded and receives a threaded plunger 186 which has a split arrowhead latch configuration 188 at its rear end and also carries twin diametrically-opposed slots 188 down its sides. The plunger passes through an aperture in the drive plate 176 and is threadedly engaged with the drive gear 184, but prevented from rotation by twin keys 190 in the aperture which engage with the slots 188. The spring plate 176 also has twin forwardly projecting lugs 192 which are designed to enter into the recesses 135 in the syringe housing when the syringe assembly is inserted to unlatch the latches 137 to unlatch the rearward collar 130 of the syringe shield 126, and therefore the syringe 114. Also, forwardly of the lug, in the opening 162 at the front of the housing are provided diametrically opposed longitudinal ribs 192 which engage the slots 139 and 127 as the syringe assembly is pushed rearwardly. At the rear ends of the ribs, as seen more clearly in FIG. 16, there are upstanding projections 194 which, as the syringe assembly is pushed rearwardly home, engage the projections 129 on the rigid shield remover 131 so that the rigid shield remover and the rigid shield 122 are arrested as the remainder of the syringe assembly is pushed home, thereby easing the rigid needle shield off the needle ready for use. The upstanding projections 194 have magnets associated therewith to retain the rigid needle shield remover against forward movement after removal of the rigid needle shield but before the injection. Thus, the loading the syringe assembly into the drive unit charges the drive mechanism, unlocks the syringe in the syringe assembly, and removes the rigid needle shield 122 in a single user action.

In operation, a syringe assembly is inserted into the opening 162 of the main unit and pushed rearwardly. This pushes the arming plate 164 rearwardly and this linear motion is converted to rotary motion to wind the constant torque spring 182 by means of an input transmission made up of the arming plate 164, the slip disk 170, the screw 172 and the shaft portion 176. As the band of the spring 182 is wrapped around the shaft 178, the spring is stressed both due to unwinding from the drive gear 184 and wrapping it around the shaft 178. As the band unwinds from the drive gear 184, the drive gear rotates and, due to the threaded engagement, the plunger 186 retracts.

At the end of the arming stroke, the plunger 186 has retracted sufficiently for the split arrowheads 188 to pass into and locate in a firing latch recess 196, and the collar 130 inside the syringe assembly has been unlatched to free the syringe, and the rigid needle shield 122 removed. Also, shortly after the arrowheads 188 have latched, the arming plate rearward movement shifts the slip disk rearwardly out of engagement with the screw 172, so it is parked over the plain part 173 so that, when the device is fired, the screw 172 can rotate freely, uncoupled from the slip disk 170.

The user disposes of the ejected rigid needle shield 122 and then offers the device up to the injection site. The injection is initiated by pressing a firing button 198 which releases the plunger 186 for forward movement so that the constant torque energy stored in the constant torque spring 182 rotates the drive gear 184 to drive the plunger forwardly so that it initially moves the syringe forward until the springs 132 bottom out whereupon effective arrest of the syringe means that the plunger now moves the piston 118 down the body of the syringe to expel a dose. Upon removal of the device from the injection site, the forward and rearward parts 128, 138 of the syringe shield both move forward under the influence of the compressed spring portions to shield the needle. As this happens, the syringe effectively moves rearwardly relative to the syringe housing 138 to return to its original rearmost position. Depending on the application, the barbs 137 may re-latch in the recesses 135 to lock the syringe in its rearmost position. Continued movement of the device away from the injection site allows a return spring (not shown) to move the arming plate forwardly to return the arming plate 164 to its original forward position, with the captive but disengaged slip disk 170 turning as it runs down the screw 172, with the screw not turning.

As in the previous embodiment, the spring is charged by an input transmission coupling that converts the insertion movement of the syringe assembly into rotary motion to charge the drive spring. An output transmission coupling then converts the stored energy in the spring to a linear motion to extend the syringe and expel and dose.

An important benefit of both arrangements is that, because the input and output transmission couplings are different, a mechanical leverage effect can be applied. Thus, the penetration and injection phases may typically require a plunger to move about 6 cm, applying quite a strong force, whilst the arming/priming/charging motion may be applied over a rather longer stroke and at a lesser force. This is not only useful for those who have a weak grip but also as an important psychological advantage in that a user may be comforted by the force necessary to arm the device is relatively low.

It will be appreciated also that these embodiments illustrate that the designer has flexibility in determining which components reside in the reusable main unit and which are disposable.

It will be appreciated that the second embodiment could be modified to use a torsion spring instead of the constant torque motor. Also both embodiments could be modified to make use of a linear rather than a rotary energy source, for example a compression or tension spring that is charged by insertion of a disposable syringe assembly.

A further potential advantage of having separate input and output transmission couplings is that the force:displacement characteristics can be adjusted. Thus if a conventional torsion or compression spring is used obeying Hooke's Law with the resultant reduction in torque/force towards the end of its movement, the pitch of the thread may be modified so that a generally constant linear thrust is applied to the syringe piston. Of course the displacement:force characteristics may be tuned to provide other functions.

The invention claimed is:

1. An autoinjector, comprising:
a housing for receiving in use in a longitudinal loading direction a syringe assembly comprising a syringe carrier and a syringe, the syringe including a syringe body having a slideable internal piston for expressing a dose contained in the body through a needle at a forward end thereof;
a drive mechanism for providing drive for operation of the autoinjector and being disposed within said housing and including a mechanical energy source and a winder element for being rotated to charge the mechanical energy source; and
an input transmission train operational between the syringe assembly and the winder element in use, whereby loading of said syringe assembly into said housing rotates said winder element to charge the mechanical energy source,
wherein the input transmission train includes a tooth element for moving linearly in use with the syringe assembly and engaged in a helical thread.

2. The autoinjector according to claim 1, wherein said housing includes a passage for receiving in use said syringe assembly.

3. The autoinjector according to claim 2, wherein, in use, said syringe assembly is configured to be inserted forwardly into said passage through a rear end.

4. The autoinjector according to claim 2, wherein, in use, said syringe assembly is configured to be inserted rearwardly into said passage through a front end.

5. The autoinjector according to claim 1, wherein said input transmission train includes a screw element mounted for rotation, which comprises the helical thread and is engaged by the tooth element that moves linearly in use upon insertion of said syringe assembly into said housing, whereby linear movement of the tooth element induces rotation of said screw element.

6. The autoinjector according to claim 1, wherein said mechanical energy source includes a torsion spring.

7. The autoinjector according to claim 1, wherein said mechanical energy source includes a constant torque spring.

8. The autoinjector according to claim 1, further comprising:
an output transmission train operational between said mechanical energy source and said slideable internal piston of the syringe,
wherein said output transmission train is separate from said input transmission train.

9. The autoinjector according to claim 8, wherein the overall mechanical advantage of the combined input and output transmission trains is non-unity.

10. The autoinjector according to claim 9, wherein said mechanical advantage is greater than unity.

11. The autoinjector according to claim 1, wherein upon loading of the syringe assembly in use into the autoinjector, the input transmission train is configured to be interrupted before said output transmission train becomes operational.

12. The autoinjector according to claim 1, wherein said syringe assembly includes a removable needle shield initially engaging the syringe to cover the syringe needle, and a needle shield remover that operationally moves to remove said needle shield upon loading of the syringe assembly into the autoinjector.

13. The autoinjector according to claim 1, wherein said drive mechanism includes a rotary to linear motion converter for applying linear drive to said slideable internal piston of the syringe, said rotary to linear motion converter including a threaded element having a thread of non-uniform pitch.

14. An autoinjector, comprising:
a housing for receiving, in use, in a longitudinal loading direction, a syringe assembly that includes a syringe carrier and a syringe,
the syringe including a syringe body that has a slideable internal piston for expressing a dose contained in the body through a needle at a forward end thereof;
a drive mechanism that drives an operation of the autoinjector, the drive mechanism being disposed within said housing and including a mechanical energy source and a winder element configured to be rotated to charge the mechanical energy source; and
an input transmission train, operational between the syringe assembly and winder element in use, whereby loading of said syringe assembly into said housing rotates said winder element to charge the mechanical energy source,
wherein said drive mechanism includes a rotary to linear motion converter for applying linear drive to said slideable internal piston of the syringe, said rotary to linear motion converter including a threaded element having a thread of non-uniform pitch.

15. The autoinjector according to claim 14, further comprising:

an output transmission train operational between said mechanical energy source and said slideable internal piston of the syringe, wherein said output transmission train is separate from said input transmission train.

16. The autoinjector according to claim 15, wherein the overall mechanical advantage of the combined input and output transmission trains is non-unity.

17. The autoinjector according to claim 16, wherein said mechanical advantage is greater than unity.

* * * * *